(12) United States Patent
Xu et al.

(10) Patent No.: US 12,098,114 B2
(45) Date of Patent: Sep. 24, 2024

(54) DOUBLE-TRAPEZOID STRUCTURAL MEMBER, FLUIDIZED APPARATUS AND NITRO COMPOUND HYDROGENATION REACTION PROCESS

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Jun Xu, Shanghai (CN); Siqing Zhong, Shanghai (CN); Le Zhao, Shanghai (CN); Lianghua Wu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 819 days.

(21) Appl. No.: 17/286,741

(22) PCT Filed: Oct. 17, 2019

(86) PCT No.: PCT/CN2019/111642
§ 371 (c)(1),
(2) Date: Apr. 19, 2021

(87) PCT Pub. No.: WO2020/078414
PCT Pub. Date: Apr. 23, 2020

(65) Prior Publication Data
US 2021/0371371 A1    Dec. 2, 2021

(30) Foreign Application Priority Data
Oct. 17, 2018    (CN) .......................... 201811206989.6

(51) Int. Cl.
*B01J 8/00* (2006.01)
*B01D 45/08* (2006.01)
(Continued)

(52) U.S. Cl.
CPC ............ *C07C 209/36* (2013.01); *B01D 45/08* (2013.01); *B01D 45/16* (2013.01); *B01J 8/0055* (2013.01);
(Continued)

(58) Field of Classification Search
CPC ..... C07C 209/36; C07C 211/46; B01D 45/08; B01D 45/16; B01J 8/0055; B01J 8/34;
(Continued)

(56) References Cited

U.S. PATENT DOCUMENTS

| | | |
|---|---|---|
| 5,779,989 A | 7/1998 | Tomasicchio et al. |
| 2006/0161036 A1 | 7/2006 | Beech, Jr. et al. |
| 2016/0102033 A1 | 4/2016 | Yang et al. |

FOREIGN PATENT DOCUMENTS

| | | |
|---|---|---|
| CN | 1528737 A | 9/2004 |
| CN | 1634860 A | 7/2005 |

(Continued)

*Primary Examiner* — Huy Tram Nguyen
(74) *Attorney, Agent, or Firm* — NKL Law; Allen Xue

(57) ABSTRACT

A fluidized apparatus contains a double-trapezoid structural member. These fluidized apparatuses are used in the nitro compound hydrogenation reaction process. The fluidized apparatus includes a shell, a gas distributor, and an inner chamber defined by an inner wall of said shell and an upper surface of said gas distributor, in the middle region of said inner chamber is disposed a perforated plate, the perforated plate comprise an outer edge region and a center region, assuming the opening rate of the outer edge region is A1 (the unit is %), assuming the opening rate of the center region is A2 (the unit is %), then A1/A2=0-0.95.

32 Claims, 4 Drawing Sheets

(51) Int. Cl.
*B01D 45/16* (2006.01)
*B01J 8/34* (2006.01)
*B01J 8/44* (2006.01)
*B01J 21/08* (2006.01)
*B01J 23/72* (2006.01)
*B01J 35/40* (2024.01)
*C07C 209/36* (2006.01)

(52) U.S. Cl.
CPC . *B01J 8/34* (2013.01); *B01J 8/44* (2013.01); *B01J 21/08* (2013.01); *B01J 23/72* (2013.01); *B01J 35/40* (2024.01); *B01J 2208/00115* (2013.01); *B01J 2208/00884* (2013.01)

(58) Field of Classification Search
CPC ..... B01J 8/44; B01J 21/08; B01J 23/72; B01J 35/40; B01J 2208/00115; B01J 2208/00884; B01J 2208/0084; B01J 2208/00132; B01J 8/1836; B01J 8/1872; B01J 8/24; B01J 8/08

USPC ......................................................... 422/139
See application file for complete search history.

(56) References Cited

FOREIGN PATENT DOCUMENTS

| | | |
|---|---|---|
| CN | 1658965 A | 8/2005 |
| CN | 1714924 A | 1/2006 |
| CN | 101016247 A | 8/2007 |
| CN | 101912753 A | 12/2010 |
| CN | 202460598 U | 10/2012 |
| CN | 104587911 A | 5/2015 |
| CN | 204865839 U | 12/2015 |
| CN | 107930540 A | 4/2018 |
| CN | 108602036 A | 9/2018 |
| EP | 3868465 A1 | 8/2021 |
| GB | 1321715 A | 6/1973 |
| RU | 2441697 C2 | 2/2012 |
| TW | 201039913 A | 11/2010 |
| WO | 2005023425 A1 | 3/2005 |

DOUBLE-TRAPEZOID STRUCTURAL MEMBER, FLUIDIZED APPARATUS AND NITRO COMPOUND HYDROGENATION REACTION PROCESS

TECHNICAL FIELD

The present invention relates to a fluidized apparatus, especially a fluidized bed reactor. The present invention also relates to a double-trapezoid structural member and a fluidized apparatus containing the double-trapezoid structural member. The present invention further relates to use of these fluidized apparatuses in the nitro compound hydrogenation reaction process.

BACKGROUND TECHNOLOGY

Aniline is an important basic organic chemical raw material and a fine chemical intermediate, can be used in producing more than 300 downstream products, and is widely used in the industries of dyes, medicines, pesticides, explosives, spices, rubbers, synthetic materials and the like. In recent years, with the rapid rise of polyurethane industry in China and worldwide, aniline, which is one of the nonreplaceable basic raw material for its main raw material MDI (4,4-diphenylmethane diisocyanate), has been developed remarkably and rapidly.

There are three commercial processes for producing aniline: nitrobenzene catalytic hydrogenation process, phenol ammoniation process and iron powder reduction process. Among others, the iron powder reduction process is gradually eliminated due to poor quality of the formed aniline. The phenol ammoniation process is strongly dependent on the source of the phenol. The current nitrobenzene catalytic hydrogenation process is adopted by most of manufacturers. The nitrobenzene catalytic hydrogenation process is also divided into a gas phase catalytic hydrogenation process and a liquid phase catalytic hydrogenation process. The nitrobenzene liquid phase catalytic hydrogenation process is firstly developed successfully by Dupont Corporation, U.S. It is mainly performed by adopting a noble metal catalyst under an anhydrous condition, and has the advantages of low reaction temperature, high catalyst load, long service life and large plant production capacity, and has the disadvantages of high required pressure, necessary separation of reactants from the catalyst and the solvent, high plant operation cost, high catalyst price, and relatively many byproducts caused by too high catalyst activity. The fluidized bed gas phase catalytic hydrogenation process is characterized by that the nitrobenzene as raw material is heated and vaporized, and mixed with hydrogen gas, then fed into the fluidized bed reactor in which the copper-silica gel catalyst is contained to perform the hydrogenation and reduction reaction.

The gas phase hydrogenation process to prepare aniline from nitrobenzene has been used in China for decades, and the fluidized bed gas phase catalytic hydrogenation process is adopted by many aniline manufacturers in China.

Chinese patent application CN1528737A discloses an apparatus, mainly comprising a fluidized bed reactor, a reaction raw material gas inlet arranged at the bottom of the reactor, a first gas distributor arranged at the upper part of the inlet, a second gas distributor arranged at the middle part of the axial-direction height of the reactor and dividing the reactor into two catalyst dense-phase zones, a heat exchanger arranged in two catalyst dense-phase zones inside the reactor; a catalyst overflow device arranged outside or inside the reactor and connecting to the upper and lower two catalyst dense-phase zones respectively, and a gas-solid separation device.

Chinese patent application CN1634860A discloses a gas distributor in a fluidized bed for aniline synthesis and a process for synthesizing aniline, wherein the gas distributor is composed of a main pipe for conveying a gas, branch pipes and an annular pipe connected thereto for distributing the gas, and nozzles for injecting the gas downwards and nozzles for injecting the gas upwards both arranged on the annular pipe.

SUMMARY OF THE INVENTION

The inventors of the present invention have found that internal structural members are prevalently arranged in the prior art fluidized bed reactor for the preparation of aniline and used for adjusting the interior gas-solid flow, but since the aniline catalyst is low in intensity and very easy to break, the particle size is gradually reduced along with the operation time, and fine powder is easily immersed into the dilute-phase zone and then the load of the cyclone separator is increased, so that the catalyst loss becomes relatively serious, and the subsequent influence is that the reaction cannot be operated for a long period, and the various problems such as the necessity of shutting down and supplementing the catalyst are caused. The inventors of the present invention have also found that due to the relatively large particle size of the aniline catalyst particles, they belong to Geldart B type particles and are not prone to fluidize. The prior art generally adjusts the fluidization quality of the bed in the reactor by adding internal structural members, but different internal structural members have different flow deflection principles and have different effects on the fluidization quality. The present invention has been completed based on these findings.

Specifically, the present invention relates to the following aspects:

1. A fluidized apparatus (especially fluidized bed reactor), comprising a shell, a gas distributor, and an inner chamber defined by an inner wall of said shell and an upper surface of said gas distributor, said inner chamber has a bottom (corresponding to the upper surface of said gas distributor) and a top, wherein along the central axis direction of said fluidized apparatus, assuming the vertical distance between the bottom and the top is H (the unit is m), the region of inner chamber from the bottom and upwards to 0.1H, 0.2H, 0.3H, 0.4H, 0.5H, 0.6H, 0.7H or 0.8H is the lower region, the region of inner chamber from the top and downward to 0.1H, 0.2H, 0.3H, 0.4H, 0.5H, 0.6H, 0.7H or 0.8H is the upper region, and the region of inner chamber between the lower region and the upper region is the middle region, the height of the middle region along the central axis direction of said fluidized apparatus is 0.005H-0.2H, 0.005H-0.05H or 0.005H-0.02H, in the middle region is disposed a perforated plate (for example selected from at least one of punched-plate, screen mesh and grid, especially grid), the perforated plate includes an outer edge region and a center region, (1) assuming the opening rate of the outer edge region is A1 (the unit is %), assuming the opening rate of the center region is A2 (the unit is %), then A1/A2=0-0.95 (preferably 0.1-0.5), or the ratio of the total opening area of the outer edge region (the unit is m2) to the total opening area of the center region (the unit is m2) is 1/10-1/2 or 1/5-1/2.

2. The fluidized apparatus according to any of abovementioned or the afterward-mentioned aspects, wherein the upper region corresponds to a dilute-phase zone, the lower region corresponds to a dense-phase zone, the middle region corresponds to a particle sputtering transition zone, and/or, the axial direction height of the perforated plate from the upper surface of said gas distributor (the unit is m) is 1.05-1.5 times or 1.05-1.2 times the axial direction height of the dense-phase zone (the unit is m).

3. The fluidized apparatus according to any of above-mentioned or the afterward-mentioned aspects, wherein the number of the perforated plate is one or more (for example 1-5, especially 1-3 or 1), and in case of more than one, the vertical distance between any two adjacent perforated plates along the central axis direction of said fluidized apparatus (the unit is m) is 0.001H-0.05H.

4. The fluidized apparatus according to any of above-mentioned or the afterward-mentioned aspects, wherein straight-line distance between any point on the peripheric edge of the perforated plate and the center point of the perforated plate is R (especially radius), the region surrounded by all points that are on the perforated plate and away from the center point by the straight-line distance of r is referred to as the center region, the region between the center region and the peripheric edge is referred to as the outer edge region, then r/R=0.2-0.99 (preferably 0.5-0.9, more preferably 0.7-0.85) or R/r=2/1-9/1, preferably 2/1-5/1.

5. The fluidized apparatus according to any of the above-mentioned or the afterward-mentioned aspects, wherein the number of opening(s) in the center region (referred to as center opening(s)) is 1-650 (preferably 5-150, more preferably 15-150)/square meter of the center region, and/or, the number of opening(s) in the outer edge region (referred to as outer edge opening(s)) is 0-4000 (preferably 100-600, more preferably 200-500)/square meter of the outer edge region, and/or, in case of more than one, the equivalent diameters for a plurality of the center openings are, identical to or different from each other, each independently 0.04-1 m, 0.04-0.5 m, or 0.04-0.1 m, and/or, in case of more than one, the equivalent diameters for a plurality of the outer edge openings are, identical to or different from each other, each independently 0.005-0.2 m, 0.005-0.08 m, or 0.005-0.03 m, and/or, the opening rate of the outer edge region is 2-40% (preferably 8-20%), the opening rate of the center region is 30-100% (preferably 40-80%), and/or, the perforated plate has a basically circle shape, the diameter of the circle is 1-10 m, preferably 2-5 m, and/or, the thickness of the perforated plate is 5-40 mm, preferably 10-35 mm.

6. The fluidized apparatus according to any of the above-mentioned or the afterward-mentioned aspects, wherein when the perforated plate is placed horizontally, the shape of the cross-section formed by cutting along the vertical direction a support body separating any two adjacent openings is selected from square, triangle, rhombus, rectangle, circle, ellipse, ring and any combination of these shapes, or the shape of the cross-section formed by cutting along the vertical direction a support body separating any two adjacent openings is such that substantially no solid particles accumulate on the surface facing towards the upper region of the support body and/or is such that solid particles in contact with the surface facing towards the lower region of the support body are substantially intercepted, or the support body is curved plate-shaped or flat plate-shaped (preferably arranged vertically or arranged inclined from the vertical direction towards the lower region (especially inclined at 0.1-60°, 5-30° or 10-20°)).

7. The fluidized apparatus according to any of the above-mentioned or the afterward-mentioned aspects, wherein the outer edge region and the center region are coaxial with the central axis of the fluidized apparatus, and/or, the peripheric edge of the perforated plate conforms to the shape of the inner wall of the shell of the middle region, and is fixed or connected to the inner wall of said shell, and/or, the peripheric edge of the perforated plate is airtightly combined with the inner wall of the shell of the middle region.

8. The fluidized apparatus according to any of the above-mentioned or the afterward-mentioned aspects, wherein the H is 5-60 m (preferably 10-30 m), and/or, the diameter of the lower region is 0.5-12 m (preferably 1-8 m), and/or, the diameter of the middle region is 0.5-16 m (preferably 1-10 m).

9. The fluidized apparatus according to any of the above-mentioned or the afterward-mentioned aspects, which further comprises a gas-solid separation device (for example cyclone separator) disposed in the upper region and a heat-exchanging device (for example heat-exchanging pipe) disposed in the lower region, and optionally comprises a double-trapezoid structural member disposed in the lower region.

10. The fluidized apparatus according to any of the above-mentioned or the afterward-mentioned aspects, wherein the double-trapezoid structural member comprises an upper baffle plate, a lower baffle plate and a connecting piece for relatively fixing the upper baffle plate and the lower baffle plate, the longitudinal section of the upper baffle plate along its central axis is a trapezoid (referred to as first trapezoid), the upper base (relatively long base) and the lower base (relatively short base) of the first trapezoid are mouth-opened, two side edges (legs) mutually form an included angle to each other, the longitudinal section of the lower baffle plate along its central axis is a trapezoid (referred to as second trapezoid), the upper base (relatively short base) and the lower base (relatively long base) of the second trapezoid are mouth-opened, two side edges (legs) mutually form an included angle to each other, the opened mouth of the lower base of the first trapezoid and the opened mouth of the upper base of the second trapezoid are nested with each other (preferably the opened mouth of the upper base of the second trapezoid is nested in the opened mouth of the lower base of the first trapezoid).

11. The fluidized apparatus according to any of the above-mentioned or the afterward-mentioned aspects, wherein the central axis of the upper baffle plate is coaxial with the central axis of the lower baffle plate, and/or, the included angle ($\alpha$) of the two side edges of the upper baffle plate is in the range of 0-120° (preferably 0-60°), the included angle ($\beta$) of the two side edges of the lower baffle plate is in the range of 0-120° (preferably 45-90°), and/or, the ratio of the length of the relatively short base of the upper baffle plate to the length of the relatively short base of the lower baffle plate is greater than 1 (preferably 1.1-3), and/or, the vertical distance between the relatively short base of the lower baffle plate and the relatively short base of the upper baffle plate (the unit is mm) is 0 to less than H1 (preferably 0.01H1 to 0.5H1), wherein H1 is the height of the first trapezoid (the unit is mm), and/or, the height of the first trapezoid H1 is 20-150 mm, the height of the second trapezoid H2 is 20-150 mm.

12. The fluidized apparatus according to any of the above-mentioned or the afterward-mentioned aspects, wherein a confined or unconfined curved surface is formed by the rotation of the two side edges of the upper baffle plate relative to its central axis, a confined or unconfined curved surface is formed by the rotation of the two side edges of the lower baffle plate relative to its central axis, and/or, the opening rate of the curved surface of the upper baffle plate is 10-50%, the opening rate of the curved surface of the lower baffle plate is 3-30%, Or, The two side edges of the upper baffle plate extend along its length direction to form two side faces, the two side edges of the lower baffle plate extend along its length direction to form two side faces, and/or, the opening rate of at least one (preferably two) of the two side faces of the upper baffle plate is 10-50%, the opening rate of at least one (preferably two) of the two side faces of the lower baffle plate is 3-30%, and/or, the size of the upper baffle plate along its length direction is 30-250 mm, the size of the lower baffle plate along its length direction is 30-250 mm.

13. The fluidized apparatus according to any of the above-mentioned or the afterward-mentioned aspects, wherein when the number of the double-trapezoid structural member(s) is more than one (for example 4-240, preferably 10-120), a plurality of the double-trapezoid structural member can be all positioned in the same horizontal plane, each and every positioned in different horizontal planes or any combination thereof, and/or, the included angle in the length direction between any two of the double-trapezoid structural members positioned in different horizontal planes and adjacent to each other in the vertical direction (γ) is 30-90°, and/or, the vertical distance between any two of the double-trapezoid structural members positioned in different horizontal planes and adjacent to each other in the vertical direction H3 is not less than 100 mm, and/or, the horizontal distance between any two adjacent double-trapezoid structural members positioned in the same horizontal plane H4 is not less than 80 mm.

14. A double-trapezoid structural member, comprising an upper baffle plate, a lower baffle plate and a connecting piece for relatively fixing the upper baffle plate and the lower baffle plate, the longitudinal section of the upper baffle plate along its central axis is a trapezoid (referred to as first trapezoid), the upper base (relatively long base) and lower base (relatively short base) of the first trapezoid are mouth-opened, two side edges (legs) mutually form an included angle to each other, the longitudinal section of the lower baffle plate along its central axis is a trapezoid (referred to as second trapezoid), the upper base (relatively short base) and the lower base (relatively long base) of the second trapezoid are mouth-opened, two side edges (legs) mutually form an included angle to each other, the opened-mouth of the lower base of the first trapezoid and the opened mouth of the upper base of the second trapezoid are nested with each other (preferably the opened mouth of the upper base of the second trapezoid is nested in the opened-mouth of the lower base of the first trapezoid).

15. The double-trapezoid structural member according to any of the above-mentioned or the afterward-mentioned aspects, wherein the central axis of the upper baffle plate is coaxial with the central axis of the lower baffle plate, and/or, the included angle (α) of the two side edges of the upper baffle plate is in the range of 0-120° (preferably 0-60°), the included angle (β) of the two side edges of the lower baffle plate is in the range of 0-120° (preferably 45-90°), and/or, the ratio of the length of the relatively short base of the upper baffle plate to the length of the relatively short base of the lower baffle plate is greater than 1 (preferably 1.1-3), and/or, the vertical distance between the relatively short base of the lower baffle plate and the relatively short base of the upper baffle plate (the unit is mm) is 0 to less than H1 (preferably 0.01H1 to 0.5H1), wherein H1 is the height of the first trapezoid (the unit is mm), and/or, the height of the first trapezoid H1 is 20-150 mm, the height of the second trapezoid H2 is 20-150 mm.

16. The double-trapezoid structural member according to any of the above-mentioned or the afterward-mentioned aspects, wherein a confined or unconfined curved surface is formed by the rotation of the two side edges of the upper baffle plate relative to its central axis, a confined or unconfined curved surface is formed by the rotation of the two side edges of the lower baffle plate relative to its central axis, and/or, the opening rate of the curved surface of the upper baffle plate is 10-50%, the opening rate of the curved surface of the lower baffle plate is 3-30%, Or, The two side edges of the upper baffle plate extend along its length direction to form two side faces, the two side edges of the lower baffle plate extend along its length direction to form two side faces, and/or, the opening rate of at least one (preferably two) of the two side faces of the upper baffle plate is 10-50%, the opening rate of at least one (preferably two) of the two side faces of the lower baffle plate is 3-30%, and/or, the size of the upper baffle plate along its length direction is 30-250 mm, the size of the lower baffle plate along its length direction is 30-250 mm.

17. A a fluidized apparatus (especially fluidized bed reactor), comprising a shell, a gas distributor, and an inner chamber defined by an inner wall of said shell and an upper surface of said gas distributor, wherein in said inner chamber is disposed the double-trapezoid structural member according to any of the above-mentioned or the afterward-mentioned aspects.

18. A nitro compound hydrogenation reaction process, comprising a step of contacting a nitro compound (especially nitrobenzene) as the reaction raw material and hydrogen gas with a hydrogenation catalyst to obtain a reaction product (for example an amino compound, especially aniline) (referred to as a hydrogenation reaction step), wherein the hydrogenation reaction step is carried out in the fluidized bed reactor according to any of the above-mentioned or the afterward-mentioned aspects.

19. The hydrogenation reaction process according to any of the above-mentioned or the afterward-mentioned aspects, wherein the reaction conditions of the hydrogenation reaction step comprise: the superficial gas velocity is 0.2-0.8 m/s, the molar ratio of hydrogen gas to the reaction raw material (for example nitrobenzene) is 6-21, the reaction temperature is 220-280° C., the reaction pressure is 0.05-MPa (gauge pressure), the hydrogenation catalyst is selected from at least one of a copper-based loaded catalyst, a nickel-based loaded catalyst and a noble metal-based loaded catalyst, and/or, the bulk density of the hydrogenation catalyst is 300-1200 kg/m3, and/or, the average particle diameter of the hydrogenation catalyst is 30-800 μm (preferably 40-500 μm or 50-600 μm), and catalyst particles having a particle diameter of less than 80 μm comprise not less than 2 wt % (preferably 5-15 wt %) by mass percent of all catalyst particles, and/or, the nitro compound is selected from at least one of the compounds represented by the following formula (1),f $$R-NO_2 \tag{1}$$

In the structural formula (1), R is an optionally substituted C2-20 straight, branched or cyclic hydrocarbyl (preferably an optionally substituted C4-20 cyclic hydrocarbyl, especially an optionally substituted C6-20 aryl, more especially an optionally substituted phenyl).

On there hand hand, the present invention relates to the following aspects:

1. An reaction apparatus for producing aniline by the hydrogenation of nitrobenzene, comprising: a fluidized bed reactor (3), a gas distributor (2), a sputtering separation structural member (6), a cyclone separator (9) and a heat-exchanging pipe (11), wherein the gas distributor (2), the sputtering separation structural member (6), the cyclone separator (9) and the heat-exchanging pipe (11) are all disposed in the fluidized bed reactor (3), in the fluidized bed reactor (3) are included a dense phase reaction zone (4) located in the lower section, a particle sputterring transition zone (5) located in the middle section and a dilute-phase zone located in the upper section (7).

2. The reaction apparatus for producing aniline by the hydrogenation of nitrobenzene according to any of the above-mentioned or the afterward-mentioned aspects, which is characterized in that in the particle sputtering transition zone (5) is disposed the sputtering separation structural member (6), the sputtering separation structural member (6) comprises a thin passage zone located at the centre region and a dense passage zone disposed at the periphery and surrounding the thin passage zone.

3. The reaction apparatus for producing aniline by the hydrogenation of nitrobenzene according to any of the above-mentioned or the afterward-mentioned aspects, which is characterized in that the ratio of the size of the passage of the dense passage zone to the area of the passage of the thin passage zone is 1/10-1/2, the preferred area ratio is 1/5-1/2.

4. The reaction apparatus for producing aniline by the hydrogenation of nitrobenzene according to any of the above-mentioned or the afterward-mentioned aspects, which is characterized in that the equivalent diameter of the passage of the dense passage zone is 0.005-0.08 m, preferably 0.005-0.03 m.

5. The reaction apparatus for producing aniline by the hydrogenation of nitrobenzene according to any of the above-mentioned or the afterward-mentioned aspects, which is characterized in that the dense passage zone and the thin passage zone are both comprised of circular plate having evenly distributed holes, a plurality of concentric annular plates that are intervally distributed, or a plurality of straight plates that are intervally and parallel disposed, vertical or inclined at a certain angle.

6. the reaction apparatus for producing aniline by the hydrogenation of nitrobenzene according to any of the above-mentioned or the afterward-mentioned aspects, which is characterized in that the dense passage zone is in form of circle, the thin passage zone is in form of circular ring, and the ratio of the diameter of the dense passage zone to the width of the thin passage zone is 2/1-9/1, preferably the ratio of diameter to width is 2/1-5/1.

7. The reaction apparatus for producing aniline by the hydrogenation of nitrobenzene according to any of the above-mentioned or the afterward-mentioned aspects, which is characterized in that the sputtering separation structural member (6), in an amount of at least one, is distributed along the axial direction of the fluidized bed reactor (3).

8. The reaction apparatus for producing aniline by the hydrogenation of nitrobenzene according to any of the above-mentioned or the afterward-mentioned aspects, which is characterized in that the axial direction height of the sputtering separation structural member (6) away from the gas distributor (2) at the bottom is 1.05-1.5 times, preferably 1.05-1.2 times the axial direction height of the dense phase reaction zone (4).

9. A reaction process for producing aniline by the hydrogenation of nitrobenzene, which uses the apparatus according to any of the above-mentioned or the afterward-mentioned aspects, comprising the following steps:

(a). Vaporized nitrobenzene and hydrogen gas as raw material are introduced into a gas chamber, then into the fluidized bed reactor (3) through the gas distributor (2) to push the catalyst in the reactor to be fluidized, then react in the dense-phase zone (4) to produce an aniline product;

(b). A part of the gas phase forms bubbles, the particle sputtering occurs at the top of the dense phase reaction zone (4) to form a particle sputtering transition zone (5), the sputtered particles are efficiently intercepted by the sputtering separation structural member (6) and return to the dense phase reaction zone (4) to proceed with the catalysis;

(c). A small part of the non-intercepted particles pass through the passage of the sputtering separation structural member (6) and enter the dilute-phase zone (7) to be separated with a cyclone separator (9), the particles return to the dense phase reaction zone (4), the crude product gas (8) flows out of the fluidized bed reactor (3) and is sent into the subsequent separation section.

10. A reaction process for producing aniline by the hydrogenation of nitrobenzene according to any of the above-mentioned or the afterward-mentioned aspects, which is characterized in that the catalyst is a metal loaded catalyst with copper as the active component, the support is alumina or silica, the catalyst has an average particle diameter of 50-600 μm; the content of catalyst particles less than 80 μm is not less than 2 wt %; the reaction conditions comprise: the superficial gas velocity in the fluidized bed reactor (3) is 0.2-0.8 m/s, the molar ratio of hydrogen gas to nitrobenzene is 6-21, the average reaction temperature in the dense phase reaction zone (4) is controlled at 220-280° C., the temperature in the vicinity of the gas distributor (2) is controlled at 320° C. or less, the reaction pressure in the dense phase reaction zone (4) is 0.05-1 MPa.

Technical Effect

According to the fluidized apparatus of the present invention, the catalyst loss is effectively reduced (for example, reduced by 30% or more).

According to the fluidized apparatus of the present invention, the gas-solid contact effect is good, the growth of large bubbles can be suppressed, and the "air cushion" generated under the commonly used flow-guiding internal structural member is overcome. Compared with the prior art, the fluidization quality in the fluidized bed is remarkably improved.

BRIEF DESCRIPTION OF THE DRAWINGS

In FIG. 1, 1: raw material of vaporized nitrobenzene and hydrogen gas; 2: gas distributor; 3: fluidized bed reactor; 4: dense-phase zone; 5: particle sputtering transition zone; 6: perforated plate; 7: dilute-phase zone; 8: crude product gas; 9: cyclone separator; 10: dipleg; 11: heat-exchanging pipe; H represents the vertical distance between the bottom and the top of the fluidized bed reactor. The peripheric edge of the perforated plate 6 is airtightly combined with the inner wall of the shell of the particle sputtering transition zone 5.

Figure 1:
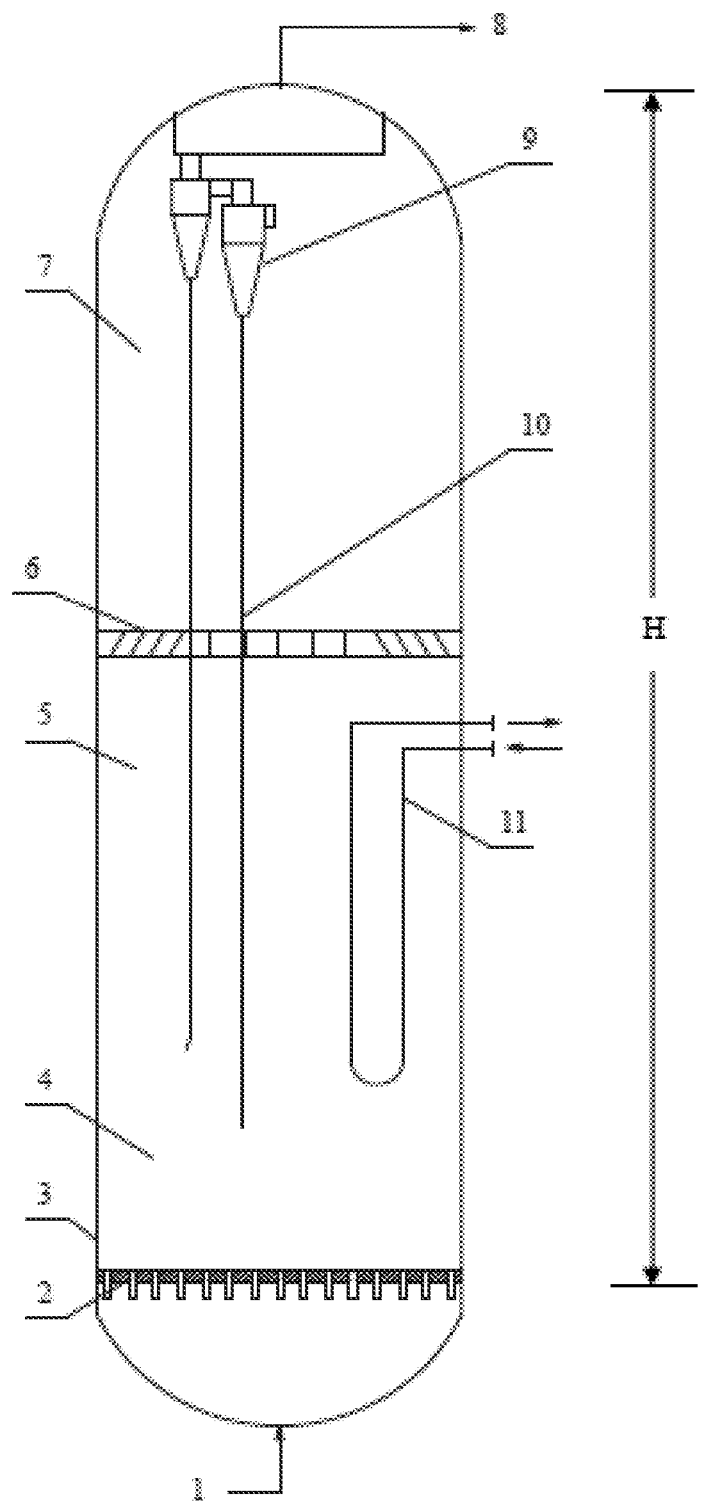
FIG. 1 is a schematic diagram of the fluidized apparatus according to one embodiment of the present invention, taking the fluidized bed reactor for producing aniline by the hydrogenation of nitrobenzene as an example.

Vaporized nitrobenzene and hydrogen gas as raw material are introduced into a gas chamber, then into the fluidized bed reactor 3 through the gas distributor 2 to push the catalyst in the reactor to be fluidized, then react in the dense-phase zone 4 to produce an aniline product, a part of the gas phase forms bubbles, the particle sputtering occurs at the top of the dense-phase zone 4 to form a particle sputtering transition zone 5, the sputtered particles are efficiently intercepted by the perforated plate 6 and return to the dense-phase zone 4 to proceed with the catalysis; a small part of the non-intercepted particles pass through the opening(s) of the perforated plate 6 and enter the dilute-phase zone 7 to be separated with a cyclone separator 9, the particles return to the dense-phase zone 4, the crude product gas 8 flows out of the fluidized bed reactor 3 and is sent into the subsequent separation section.

Figure 2:
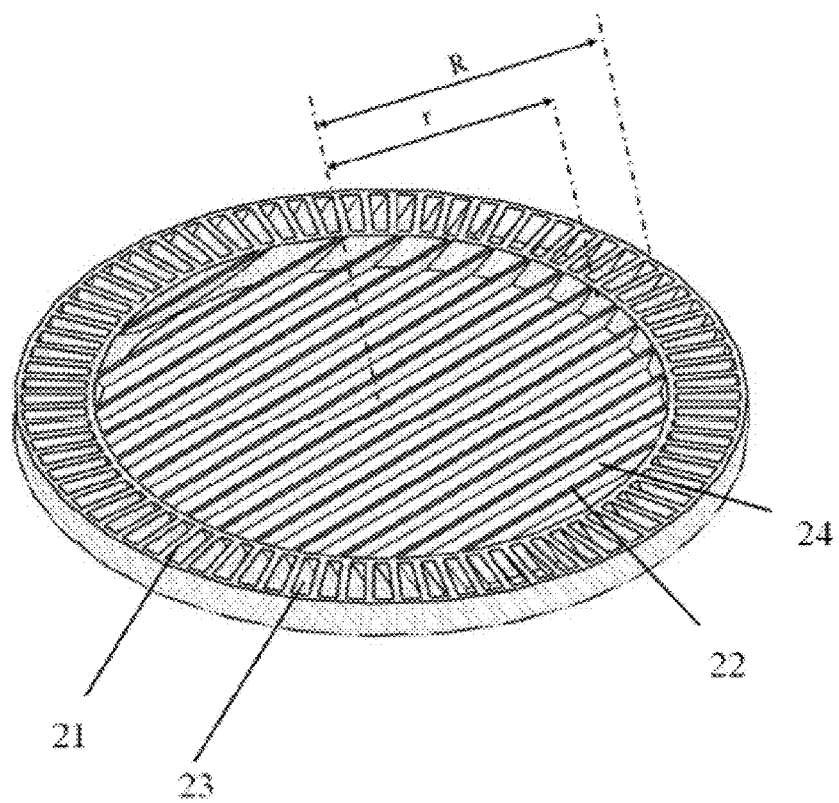

FIG. 2 is a three-dimensional schematic diagram of the perforated plate according to one embodiment of the present invention.

In FIG. 2, 21 is the support body of the outer edge region (inclined with respect to a horizontal plane), 23 is the opening of the outer edge region (inclined with respect to a horizontal plane), 22 is the support body of the center region (inclined with respect to a horizontal plane), 24 is the opening of the center region (inclined with respect to a horizontal plane).

Figure 3:
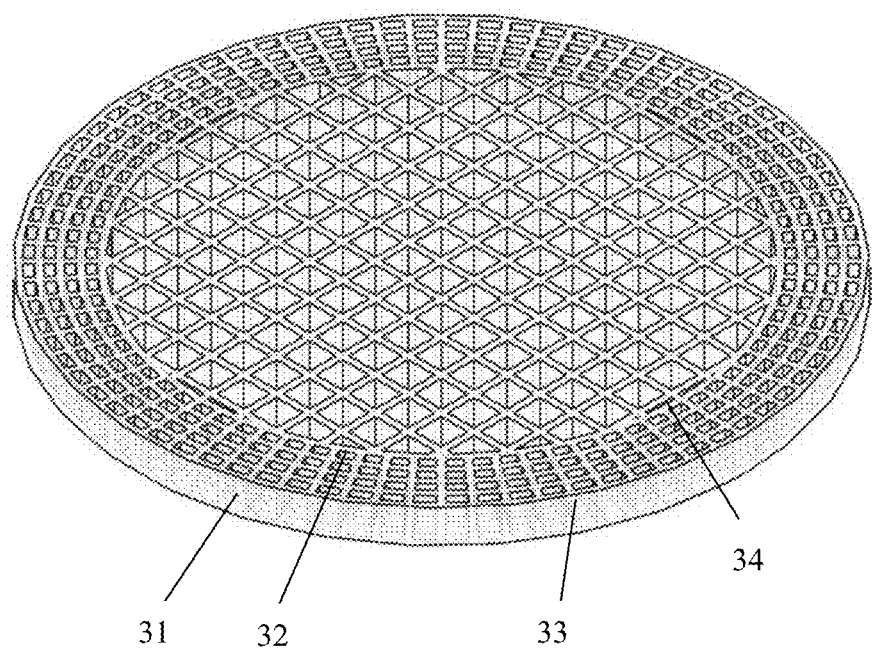

FIG. 3 is a three-dimensional schematic diagram of the perforated plate according to another embodiment of the present invention.

FIG. 3, 31 is the support body of the outer edge region (vertical with respect to a horizontal plane), 33 is the opening of the outer edge region (vertical with respect to a horizontal plane), 32 is the support body of the center region (vertical with respect to a horizontal plane), 34 is the opening of the center region (vertical with respect to a horizontal plane).

Figure 4:
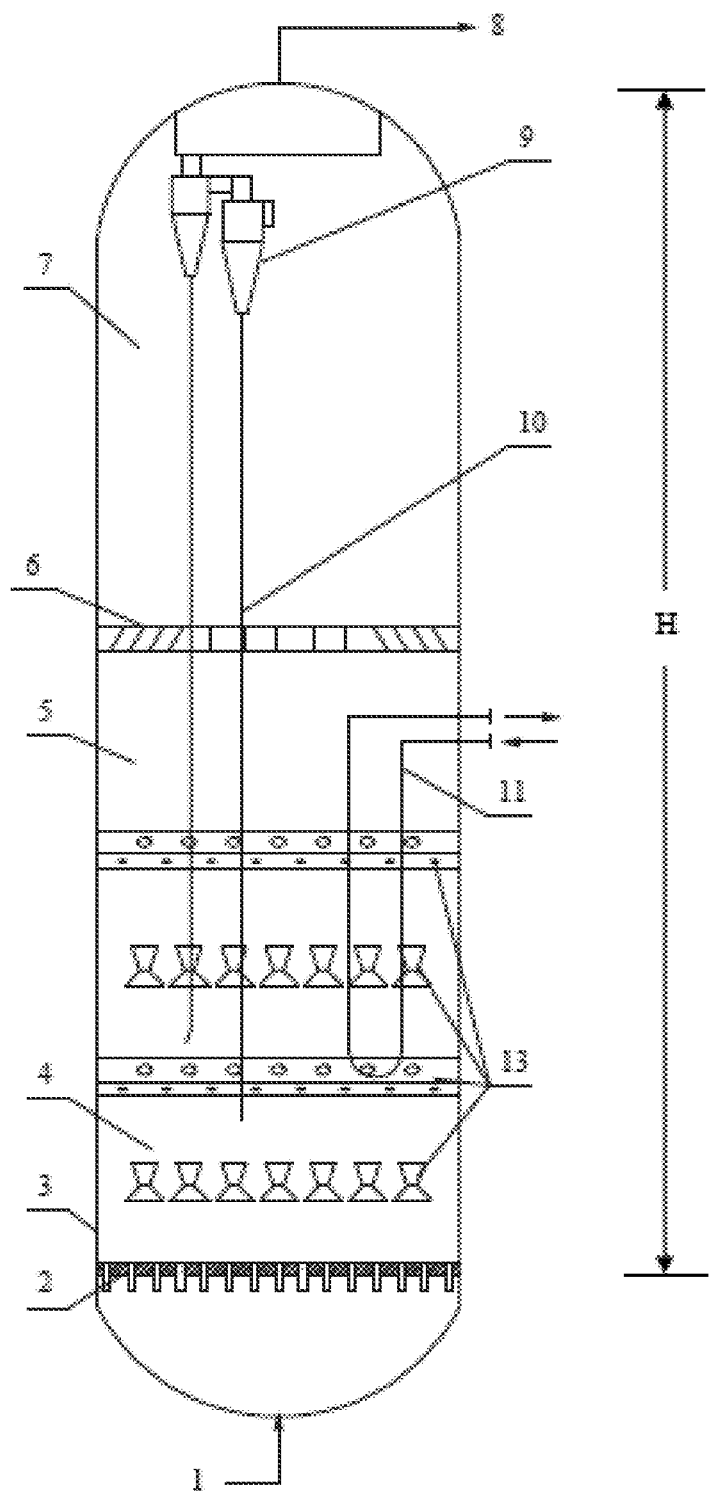

FIG. 4 is a schematic diagram of the fluidized apparatus according to another embodiment of the present invention, taking the fluidized bed reactor for producing aniline by the hydrogenation of nitrobenzene as an example.

In FIG. 4, 1: raw material of vaporized nitrobenzene and hydrogen gas; 2: gas distributor; 3: fluidized bed reactor; 4: dense-phase zone; 5: particle sputtering transition zone; 6: perforated plate; 7: dilute-phase zone; 8: crude product gas; 9: cyclone separator; 10: dipleg; 11: heat-exchanging pipe; 13: double-trapezoid structural member (4 layers in the Figure); H represents the vertical distance between the bottom and the top of the fluidized-bed reaction. The peripheric edge of the perforated plate 6 is airtightly combined with the inner wall of the shell of the particle sputtering transition zone 5.

Vaporized nitrobenzene and hydrogen gas as raw material are introduced into a gas chamber, then into the fluidized bed reactor 3 through the gas distributor 2 to push the catalyst in the reactor to be fluidized, when flowing through the double-trapezoid structural member 13, under the action of the double-trapezoid structural member 13, the agglomerates formed by the catalyst and gradually growing bubbles are effectively broken, and the broken gas and catalyst particles are ejected from the holes/slits of the double-trapezoid structural member 13, the gas and the solid in the dense-phase zone 4 of the fluidized bed reactor 3 are evenly mixed with a uniform temperature distribution, then react in the dense-phase zone 4 to produce an aniline product; a part of the gas phase forms bubbles, the particle sputtering occurs at the top of the dense-phase zone 4 to form a particle sputtering transition zone 5, the sputtered particles are efficiently intercepted by the perforated plate 6 and return to the dense-phase zone 4 to proceed with the catalysis; a small part of the non-intercepted particles pass through the opening(s) of the perforated plate 6 and enter the dilute-phase zone 7 to be separated with a cyclone separator 9, the particles return to the dense-phase zone 4, the crude product gas 8 flows out of the fluidized bed reactor 3 and is sent into the subsequent separation section.

Figure 5:
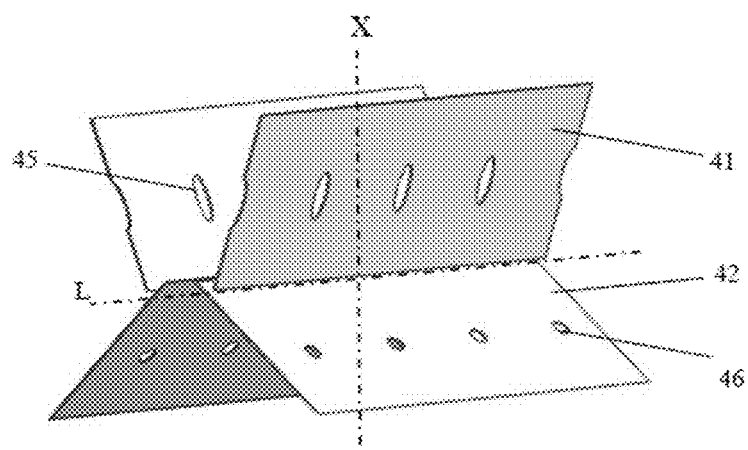

FIG. 5 is a three-dimensional schematic diagram of the double-trapezoid structural member according to one embodiment of the present invention.

In FIG. 5, 41: the upper baffle plate, 42: the lower baffle plate, the opened mouth of the upper base of the lower baffle plate is nested in the opened mouth of the lower base of the upper baffle plate, 45: the opening of the upper baffle plate (for example hole or slit), 46: the opening of the lower baffle plate (for example hole or slit), X represents the central axis of the double-trapezoid structural member, L represents the two-way length direction (also known as major axis) of the double-trapezoid structural member. The connecting piece is not shown in the Figure.

Figure 6:
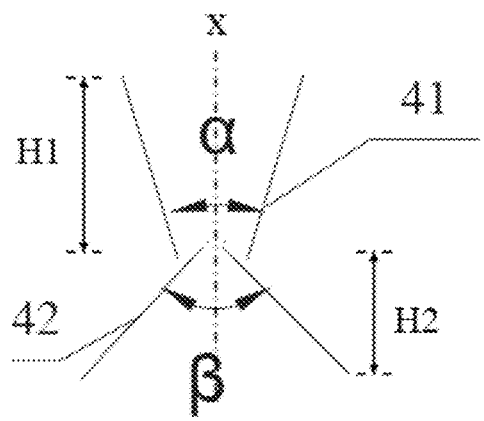

FIG. 6 is a schematic diagram of the longitudinal section of the double-trapezoid structural member according to one embodiment of the present invention.

In FIG. 6, 41: the upper baffle plate, 42: the lower baffle plate, the opened mouth of the upper base of the lower baffle plate is nested in the opened mouth of the lower base of the upper baffle plate, $\alpha$: the included angle of two side edges of the upper baffle plate 41, $\beta$: the included angle of two side edges of the lower baffle plate 42, X represents the central axises of two baffles (superposition), H1 is the height of the first trapezoid, H2 is the height of the second trapezoid. The connecting piece is not shown in the Figure.

Figure 7:
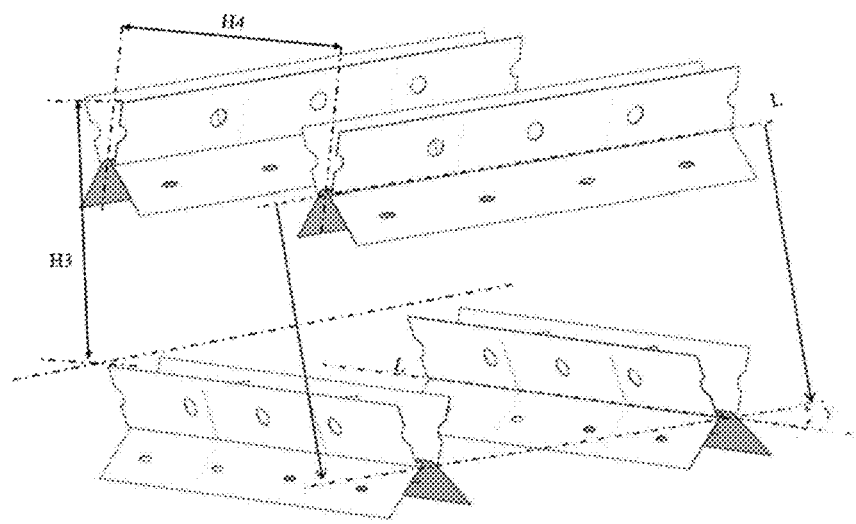

FIG. 7 is a schematic diagram of the positional relationship of a plurality of double-trapezoid structural members according to the present invention.

In FIG. 7, $\gamma$ is the included angle in the length direction between any two double-trapezoid structural members positioned in different horizontal planes and adjacent to each other in the vertical direction; L represents the two-way major axis of each double-trapezoid structural member; H3 represents the vertical distance between any two of the double-trapezoid structural members positioned in different horizontal planes and adjacent to each other in the vertical direction; H4 represents the horizontal distance between any two adjacent double-trapezoid structural members positioned in the same horizontal plane. The connecting piece is not shown in the Figure.

DETAILED DESCRIPTION

Reference will now be made in detail to the present embodiments of the present invention, but it should be understood that the scope of the invention is not limited by the embodiments, but is defined by the appended claims.

All publications, patent applications, patents, and other references mentioned in this specification are herein incorporated by reference in their entirety. Unless defined otherwise, all technical and scientific terms used herein have the same meanings as commonly understood by those skilled in the art to which this invention belongs. In case of conflict, the present specification, including definitions, will control.

When the specification derives a material, a substance, a process, a step, a device, an element and the like with the expression such as "known to those skilled in the art", "prior art", or the anologous term, it is intended that the subject matter so derived encompasses those having been conventionally used in the art at the time of filing this application, but also includes those which may not be so commonly used at the present time, but will become known in the art as being suitable for a similar purpose.

In the context of the present specification, the term "substantially" means the allowance of the presence of a deviation acceptable to those skilled in the art or considered reasonable by those skilled in the art, for example, a deviation within ±10%, within ±5%, within ±1%, within ±0.5% or within ±0.1%.

In the context of the present specification, the expression "optionally substituted" refers to optionally substituted by one or more (for example 1-5, 1-4, 1-3, 1-2 or 1) substituent groups selected from halogen, hydroxy, mercapto, amino, aminocarbonyl, nitro, oxo, thio, cyano, C1-6 linear or branched (halo) alkane (oxy, thio, amino, carbonyl) group, C2-6 linear or branched (halo) alkene (oxy, thio, amino, carbonyl) group, C2-6 linear or branched (halo) alkyne (oxy, thio, amino, carbonyl) group, C3-20 cycloalkyl, C3-20 cycloalkane (oxy, thio, amino) group, C3-20 cycloalkyl C1-6 linear or branched (halo) alkane (oxy, thio, amino, carbonyl) group, C3-20 cycloalkyl C2-6 linear or branched (halo) alkene (oxy, thio, amino, carbonyl) group, C3-20 cycloalkyl C2-6 linear or branched (halo) alkyne (oxy, thio, amino, carbonyl) group, C3-20 cycloalkenyl, C3-20 cycloalkene (oxy, thio, amino) group, C3-20 cycloalkenyl C1-6 linear or branched (halo) alkane (oxy, thio, amino, carbonyl) group, C3-20 cycloalkenyl C2-6 linear or branched (halo) alkene (oxy, thio, amino, carbonyl) group, C3-20 cycloalkenyl C2-6 linear or branched (halo) alkyne (oxy, thio, amino, carbonyl) group, C6-20 aryl, C6-20 arene (oxy, thio, amino) group, C6-20 aryl C1-6 linear or branched (halo) alkane (oxy, thio, amino, carbonyl) group, C6-20 aryl C2-6 linear or branched (halo) alkene (oxy, thio, amino, carbonyl) group, C6-20 aryl C2-6 linear or branched (halo) alkyne (oxy, thio, amino, carbonyl) group, C4-20 heteroaryl, C4-20 heteroarene (oxy, thio, amino) group, C4-20 heteroaryl C1-6 linear or branched (halo) alkane (oxy, thio, amino, carbonyl) group, C4-20 heteroaryl C2-6 linear or branched (halo) alkene (oxy, thio, amino, carbonyl) group, C4-20 heteroaryl C2-6 linear or branched (halo) alkyne (oxy, thio, amino, carbonyl) group, C2-20 heterocyclyl, C2-20 heterocycle (oxy, thio, amino) group, C2-20 heterocyclyl C1-6 linear or branched (halo) alkane (oxy, thio, amino, carbonyl) group, C2-20 heterocyclyl C2-6 linear or branched (halo) alkene (oxy, thio, amino, carbonyl) group and C2-20 heterocyclyl C2-6 linear or branched (halo) alkyne (oxy, thio, amino, carbonyl) group. When a plurality of these substituent groups are present, two adjacent substituent groups (for example the molecular chain ends of two substituent groups) can be bonded to each other to form a divalent substituent group structure. For example, two adjacent C1-6 linear or branched alkyl groups can be bonded to each other to form a corresponding alkylene structure. Or, two adjacent C1-6 linear or branched alkyloxy groups for example can form a corresponding alkylenedioxy group structure, two adjacent C1-6 linear or branched alkylamino groups for example can form a corresponding alkylenediamino structure, two adjacent C1-5 linear or branched alkylthio groups for example can form a corresponding alkylenedithio structure, and so forth. As the preferred substituent group, for example, halogen, hydroxy, mercapto, amino, thio, oxo or C1-6 linear or branched (halo) alkane (oxy, thio, amino, carbonyl) group and others can be enumerated. Herein, the expression "(halo) alkane (oxy, thio, amino, carbonyl) group" means: alkyl, haloalkyl, alkyloxy, alkylthio, alkylamino, alkylcarbonyl, haloalkyloxy, haloalkylthio, haloalkylamino or haloalkylcarbonyl, the expression "(halo) alkene (oxy, thio, amino, carbonyl) group" means: alkenyl, haloalkenyl, alkenyloxy, alkenylthio, alkenylamino, alkenylcarbonyl, haloalkenyloxy, haloalkenylthio, haloalkenylamino or haloalkenylcarbonyl, the expression "(halo) alkyne (oxy, thio, amino, carbonyl) group" means: alkynyl, haloalkynyl, alkynyloxy, alkynylthio, alkynylamino, alkynylcarbonyl, haloalkynyloxy, haloalkynylthio, haloalkynylamino or haloalkynylcarbonyl, the expression "(oxy, thio, amino) group" means oxy, thio or amino. Here, the expression "halo" includes monohalo, dihalo, trihalo, or perhalo, and the like.

All percentages, parts, ratios, and the like referred to within this specification are by weight and pressures are gauge pressures unless explicitly indicated.

In the context of this specification, any two or more embodiments of the present invention may be combined in any combination, and the resulting technical solution is part of the original disclosure of this specification, and is within the scope of the present invention.

According to an embodiment of the present invention, it relates to a fluidized apparatus. As the fluidized apparatus, a fluidized bed reactor can be particularly enumerated, and a fluidized bed reactor for producing aniline by the hydrogenation of nitrobenzene can be even particularly enumerated.

According to the fluidized apparatus of the present invention, upon being used in producing aniline by the hydrogenation of nitrobenzene, the catalyst loss and consumption can decrease by 30% or more.

According to an embodiment of the present invention, the fluidized apparatus comprises a shell, a gas distributor, and an inner chamber defined by an inner wall of said shell and an upper surface of said gas distributor, wherein said inner chamber has a bottom and a top. Herein, the bottom corresponds to the upper surface of said gas distributor.

According to an embodiment of the present invention, along the central axis direction of said fluidized apparatus, assuming the vertical distance between the bottom and the top is H (the unit is m), the region of inner chamber from the bottom and upwards to 0.1H, 0.2H, 0.3H, 0.4H, 0.5H, 0.6H, 0.7H or 0.8H is the lower region, the region of inner chamber from the top and downward to 0.1H, 0.2H, 0.3H, 0.4H, 0.5H, 0.6H, 0.7H or 0.8H is the upper region, and the region of inner chamber between the lower region and the upper region is the middle region, in the middle region is disposed a perforated plate. Herein, as the perforated plate, for example, at least one selected from punched-plate, screen mesh and grid, especially grid can be mentioned. For example, the H is generally 5-60 m, preferably 10-30 m, but sometimes not limited thereto. In addition, the lower region has a diameter of generally 0.5-12 m, preferably 1-8 m, but sometimes not limited thereto. Or, the middle region has a diameter of is generally 0.5-16 m, preferably 1-10 m, but sometimes not limited thereto.

According to an embodiment of the present invention, the height of the middle region along the central axis direction of said fluidized apparatus is generally 0.005H-0.2H, 0.005H-0.05H or 0.005H-0.02H.

According to an embodiment of the present invention, the upper region corresponds to the dilute-phase zone of the fluidized apparatus, the lower region corresponds to the dense-phase zone of the fluidized apparatus, the middle region corresponds to the particle sputtering transition zone of the fluidized apparatus.

According to an embodiment of the present invention, the perforated plate includes an outer edge region and a center region. Specifically speaking, assuming straight-line distance between any point on the peripheric edge of the perforated plate and the center point of the perforated plate is R, the region surrounded by all points that are on the perforated plate and away from the center point by the straight-line distance of r is referred to as the center region, the region between the center region and the peripheric edge is referred to as the outer edge region, then r/R=0.2-0.99, preferably 0.5-0.9, more preferably 0.7-0.85, or R/r=2/1-9/1, preferably 2/1-5/1. Herein, if the perforated plate is a circular disc, R is the radius of the perforated plate or the circular disc, while r is the radius of the center region. Preferably, the outer edge region and the center region are coaxial with the central axis of the fluidized apparatus. At this point, the outer edge region is ring-shaped with R-r as the width, and the center region is surrounded by the outer edge region with r as the radius.

According to an embodiment of the present invention, assuming the opening rate of the outer edge region is A1 (the unit is %), assuming the opening rate of the center region is A2 (the unit is %), then A1/A2=0-0.95, preferably 0.1-0.5. Here, the so-called "opening rate" refers to the ratio of the total area of all the openings on the perforated plate (the unit is m2) to the area of the perforated plate (the unit is m2).

According to an embodiment of the present invention, the ratio of the total opening area of the outer edge region (the unit is m2) to the total opening area of the center region (the unit is m2) is 1/10-1/2 or 1/5-1/2.

According to an embodiment of the present invention, the axial direction height of the perforated plate from the upper surface of said gas distributor (the unit is m) is 1.05-1.5 times or 1.05-1.2 times the axial direction height of the dense-phase zone (the unit is m). In the context of the present invention, unless otherwise specified, the so-called "axial direction" refers to the central axis direction of said fluidized apparatus.

According to an embodiment of the present invention, the number of the perforated plate is one or more, for example 1-5, especially 1-3 or 1. In addition, in case that the number of the perforated plate is more than one, the vertical distance between any two adjacent perforated plates along the central axis direction of said fluidized apparatus (the unit is m) is generally 0.001H-0.05H.

According to an embodiment of the present invention, the number of opening(s) in the center region (referred to as center opening(s)) is generally 1-650/square meter of the center region, preferably 5-150/square meter of the center region, more preferably 15-150/square meter of the center region.

According to an embodiment of the present invention, the number of opening(s) in the outer edge region (referred to as outer edge opening(s)) is 0-4000/square meter of the outer edge region, preferably 100-600/square meter of the outer edge region, more preferably 200-500/square meter of the outer edge region.

According to an embodiment of the present invention, in the presence of a plurality of the center openings, the equivalent diameters for a plurality of the center openings are, identical to or different from each other, each independently 0.04-1 m, 0.04-0.5 m, or 0.04-0.1 m. In addition, in the presence of a plurality of the outer edge openings, the equivalent diameters for a plurality of the outer edge openings are, identical to or different from each other, each independently 0.005-0.2 m, 0.005-0.08 m, or 0.005-0.03 m. Herein, the so-called "equivalent diameter" refers to the equivalent circle diameter.

According to an embodiment of the present invention, the opening rate of the outer edge region is generally 2-40%, preferably 8-20%. In addition, the opening rate of the center region is generally 30-100%, preferably 40-80%. Herein, the so-called "opening rate" refers to the ratio of the total area of all openings in the region (the unit is m2) to the area of the region (the unit is m2).

According to an embodiment of the present invention, the perforated plate has a basically circle shape, and the diameter of the circle is generally 1-10 m, preferably 2-5 m. Preferably, the peripheric edge of the perforated plate conforms to the shape of the inner wall of the shell of the middle region, and is fixed or connected to the inner wall of said shell. More preferably, the peripheric edge of the perforated plate is airtightly combined with the inner wall of the shell of the middle region. Herein, the so-called "airtightly combined with" refers to that the entire peripheric edge of the perforated plate and the inner wall of the corresponding entire shell of the central region are combined together, and the combination part between the two is substantially free of pores or gaps for gas (obviously also including solid particles) to pass through the combination part. In this case, the diameter of the perforated plate is generally identical to the diameter of the middle region, whereby substantially no solid particles or gases can pass through the combination part between the peripheric edge of the perforated plate and the inner wall of the shell of the middle region.

According to an embodiment of the present invention, the thickness of the perforated plate is generally 5-40 mm, preferably 10-35 mm.

According to an embodiment of the present invention, when the perforated plate is placed horizontally, the shape of the cross-section formed by cutting along the vertical direction a support body separating any two adjacent openings is selected from square, triangle, rhombus, rectangle, circle, ellipse, ring and any combination of these shapes.

According to an embodiment of the present invention, when the perforated plate is placed horizontally, the shape of the cross-section formed by cutting along the vertical direction a support body separating any two adjacent openings is such that substantially no solid particles accumulate on the surface facing towards the upper region of the support body and/or is such that solid particles in contact with the surface facing towards the lower region of the support body are substantially intercepted.

According to an embodiment of the present invention, when the perforated plate is placed horizontally, the support body separating any two adjacent openings is curved plate-shaped or flat plate-shaped, preferably arranged vertically or arranged inclined from the vertical direction towards the lower region. Herein, as to be arranged inclined, for example being inclined at 0.1-60°, 5-30° or 10-20° with respect to a direction perpendicular to the horizontal plane can be mentioned.

According to one embodiment of the present invention, the fluidized apparatus further comprises a gas-solid separation device (for example cyclone separator) disposed in the upper region and a heat-exchanging device (for example heat-exchanging pipe) disposed in the lower region. These gas-solid separation devices and the heat-exchanging device and the like are the conventional structural members commonly used in the fluidized apparatus, especially the fluidized bed reactor, and will not be repeated here.

With reference to FIG. 1, the fluidized bed reactor of the present invention will be described in more detail. The fluidized bed reactor comprises a fluidized bed reactor 3, a gas distributor 2, a perforated plate 6, a cyclone separator 9 and a heat-exchanging pipe 11, wherein the gas distributor 2, the perforated plate 6, the cyclone separator 9 and the heat-exchanging pipe 11 are all disposed in the fluidized bed reactor 3; in the fluidized bed reactor 3 are included a dense-phase zone 4 located in the lower section, a particle sputterring transition zone 5 located in the middle section and a dilute-phase zone 7 located in the upper section. In the particle sputtering transition zone 5 is disposed the perforated plate 6.

According to the fluidized bed reactor of the present invention, vaporized nitrobenzene and hydrogen gas as raw material are introduced into a gas chamber, then into the fluidized bed reactor 3 through the gas distributor 2 to push the catalyst in the reactor to be fluidized, then react in the dense-phase zone 4 to produce an aniline product; a part of the gas phase forms bubbles, the particle sputtering occurs at the top of the dense-phase zone 4 to form a particle sputtering transition zone 5, the sputtered particles are efficiently intercepted by the perforated plate 6 and return to the dense-phase zone 4 to proceed with the catalysis; a small part of the non-intercepted particles pass through the passage of the perforated plate 6 and enter the dilute-phase zone 7 to be separated with a cyclone separator 9, the particles return to the dense-phase zone 4, the crude product gas 8 flows out of the fluidized bed reactor 3 and is sent into the subsequent separation section.

According to one embodiment of the present invention, the fluidized apparatus further comprises a double-trapezoid structural member disposed in the lower region in order to regulate the fluidized state in the lower region and improve the fluidization quality. Herein, the double-trapezoid structural member comprises an upper baffle plate, an lower baffle plate and a connecting piece for relatively fixing the upper baffle plate and the lower baffle plate.

According to one embodiment of the present invention, as the connecting piece, any structural style can be adopted as long as the upper baffle plate and the lower baffle plate can be relatively fixed without particular limitation, but for example, metal strip, metal rod, metal wire and metal plate can be specifically enumerated. In addition, as the connecting piece for fixing or connecting the double-trapezoid structural member relative to the lower region, the structural member of any structural format for fixing or installing the flow rectifier of the fluidized bed in the art to which the present invention belongs can be directly applied without particular limitation, but for example, metal strip, metal rod, metal wire, metal plate and the like can be specifically enumerated.

According to one embodiment of the present invention, the longitudinal section of the upper baffle plate along its central axis is a trapezoid (referred to as first trapezoid), the upper base (relatively long base) and the lower base (relatively short base) of the first trapezoid are mouth-opened, two side edges (legs) mutually form an included angle to each other, the longitudinal section of the lower baffle plate along its central axis is a trapezoid (referred to as second trapezoid), the upper base (relatively short base) and the lower base (relatively long base) of the second trapezoid are mouth-opened, two side edges (legs) mutually form an included angle to each other, the opened mouth of the lower base of the first trapezoid and the opened mouth of the upper base of the second trapezoid are nested with each other. Preferably, the opened mouth of the upper base of the second trapezoid is nested in the opened mouth of the lower base of the first trapezoid.

According to one embodiment of the present invention, the central axis of the upper baffle plate is coaxial with the central axis of the lower baffle plate.

According to one embodiment of the present invention, the included angle ($\alpha$) of the two side edges of the upper baffle plate is in the range of 0-120° (preferably 0-60°), the included angle ($\beta$) of the two side edges of the lower baffle plate is in the range of 0-120° (preferably 45-90°).

According to one embodiment of the present invention, the ratio of the length of the relatively short base of the upper baffle plate to the length of the relatively short base of the lower baffle plate is greater than 1, preferably 1.1-3.

According to one embodiment of the present invention, the vertical distance between the relatively short base of the lower baffle plate and the relatively short base of the upper baffle plate (the unit is mm) is 0 to less than H1, preferably 0.01H1 to 0.5H1. Herein, H1 is the height of the first trapezoid (the unit is mm).

According to one embodiment of the present invention, the height H1 of the first trapezoid is generally 20-150 mm, the height H2 of the second trapezoid is generally 20-150 mm.

According to one embodiment of the present invention, a confined or unconfined curved surface is formed by the rotation of the two side edges of the upper baffle plate relative to its central axis, a confined or unconfined curved surface is formed by the rotation of the two side edges of the lower baffle plate relative to its central axis.

According to one embodiment of the present invention, the opening rate of the curved surface of the upper baffle plate is 10-50%, the opening rate of the curved surface of the lower baffle plate is 3-30%. Herein, the so-called "opening rate" refers to the ratio of the total area of all openings (for example one or more pores and/or slits exist) on the curved surface (the unit is m2) to the area of the curved surface (the unit is m2).

According to one embodiment of the present invention, the two side edges of the upper baffle plate extend along its length direction to form two side faces, the two side edges of the lower baffle plate extend along its length direction to form two side faces. In the context of the present invention, unless otherwise specified, the so-called "length direction" refers to the direction perpendicular to the trapezoid plane (likewise perpendicular to the central axis).

According to one embodiment of the present invention, the opening rate of at least one (preferably two) of the two side faces of the upper baffle plate is 10-50%, the opening rate of at least one (preferably two) of the two side faces of the lower baffle plate is 3-30%. Herein, the so-called "opening rate" refers to the ratio of the total area of all openings (for example one or more pores and/or slits exist) on the side face (the unit is m2) to the area of the side face (the unit is m2).

According to one embodiment of the present invention, the size of the upper baffle plate along its length direction is generally 30-250 mm, the size of the lower baffle plate along its length direction is generally 30-250 mm.

According to one embodiment of the present invention, when the number of the double-trapezoid structural member(s) is more than one (for example 4-240, preferably 10-120), a plurality of th double-trapezoid structural members can be all positioned in the same horizontal plane, each and every positioned in different horizontal planes, or any combination thereof.

According to one embodiment of the present invention, the included angle in the length direction between any two of the double-trapezoid structural members positioned in different horizontal planes and adjacent to each other in the vertical direction ($\gamma$) is 30-90°.

According to one embodiment of the present invention, the vertical distance between any two of the double-trapezoid structural members positioned in different horizontal planes and adjacent to each other in the vertical direction H3 is not less than 100 mm. Herein, H3 refers to the vertical distance between relatively long bases of the upper baffle plates of different double-trapezoid structural members.

According to one embodiment of the present invention, the horizontal distance between any two adjacent double-trapezoid structural members positioned in the same horizontal plane H4 is not less than 80 mm. Herein, H4 refers to the vertical distance between the central axises of different double-trapezoid structural members.

According to one embodiment of the present invention, it also relates to a double-trapezoid structural member, comprising an upper baffle plate, a lower baffle plate and a connecting piece for relatively fixing the upper baffle plate and the lower baffle plate. Herein, as the connecting piece, any structural style can be adopted as long as the upper baffle plate and the lower baffle plate can be relatively fixed without particular limitation, but for example, metal strip, metal rod, metal wire and metal plate and the like can be specifically enumerated.

According to one embodiment of the present invention, the longitudinal section of the upper baffle plate along its central axis is a trapezoid (referred to as first trapezoid), the upper base (relatively long base) and the lower base (relatively short base) of the first trapezoid are mouth-opened, two side edges (legs) mutually form an included angle to each other, the longitudinal section of the lower baffle plate along its central axis is a trapezoid (referred to as second trapezoid), the upper base (relatively short base) and the lower base (relatively long base) of the second trapezoid are mouth-opened, two side edges (legs) mutually form an included angle to each other, the opened mouth of the lower base of the first trapezoid and the opened mouth of the upper base of the second trapezoid are nested with each other. Preferably, the opened mouth of the upper base of the second trapezoid is nested in the opened-mouth of the lower base of the first trapezoid.

According to one embodiment of the present invention, the central axis of the upper baffle plate is coaxial with the central axis of the lower baffle plate.

According to one embodiment of the present invention, the included angle (α) of the two side edges of the upper baffle plate is in the range of 0-120° (preferably 0-60°), the included angle (β) of the two side edges of the lower baffle plate is in the range of 0-120° (preferably 45-90°).

According to one embodiment of the present invention, the ratio of the length of the relatively short base of the upper baffle plate to the length of the relatively short base of the lower baffle plate is greater than 1, preferably 1.1-3.

According to one embodiment of the present invention, the vertical distance between the relatively short base of the lower baffle plate and the relatively short base of the upper baffle plate (the unit is mm) is 0 to less than H1, preferably 0.01H1 to 0.5H1, wherein H1 is the height of the first trapezoid (the unit is mm).

According to an embodiment of the present invention, the height H1 of the first trapezoid is generally 20-150 mm, the height H2 of the second trapezoid is generally 20-150 mm.

According to one embodiment of the present invention, a confined or unconfined curved surface is formed by the rotation of the two side edges of the upper baffle plate relative to its central axis, a confined or unconfined curved surface is formed by the rotation of the two side edges of the lower baffle plate relative to its central axis.

According to one embodiment of the present invention, the opening rate of the curved surface of the upper baffle plate is 10-50%, the opening rate of the curved surface of the lower baffle plate is 3-30%. Herein, the so-called "opening rate" refers to the ratio of the total area of all openings (for example one or more pores and/or slits exist) on the curved surface (the unit is m2) to the area of the curved surface (the unit is m2).

According to one embodiment of the present invention, the two side edges of the upper baffle plate extend along its length direction to form two side faces, the two side edges of the lower baffle plate extend along its length direction to form two side faces.

According to one embodiment of the present invention, the opening rate of at least one (preferably two) of the two side faces of the upper baffle plate is 10-50%, the opening rate of at least one (preferably two) of the two side faces of the lower baffle plate is 3-30%. Herein, the so-called "opening rate" refers to the ratio of the total area of all openings (for example one or more pores and/or slits exist) on the side face (the unit is m2) to the area of the side face (the unit is m2).

According to an embodiment of the present invention, the size of the upper baffle plate along its length direction is generally 30-250 mm, the size of the lower baffle plate along its length direction is generally 30-250 mm.

According to an embodiment of the present invention, it also relates to a fluidized apparatus, especially a fluidized bed reactor. Herein, the fluidized apparatus comprises a shell, a gas distributor, and an inner chamber defined by an inner wall of said shell and an upper surface of said gas distributor, wherein in said inner chamber is disposed a double-trapezoid structural member according to any of the embodiments as previously mentioned in the present invention as the flow rectifier. As the fluidized bed reactor, the fluidized bed reactor for producing aniline by the hydrogenation of nitrobenzene can be particularly enumerated.

According to an embodiment of the present invention, it also relates to a nitro compound hydrogenation reaction process, especially the reaction process for producing aniline by the hydrogenation of nitrobenzene. Herein, the hydrogenation reaction process comprises a step of contacting a nitro compound and hydrogen gas as the reaction raw material with a hydrogenation catalyst to obtain a reaction product (referred to as a hydrogenation reaction step), wherein the hydrogenation reaction step is carried out in the fluidized bed reactor according to any of the previous embodiments of the present invention.

According to one embodiment of the present invention, in the hydrogenation reaction step, the superficial gas velocity is generally 0.2-0.8 m/s, the molar ratio of hydrogen gas to the reaction raw material (for example nitrobenzene) is generally 6-21.

According to one embodiment of the present invention, in the hydrogenation reaction step, the reaction temperature (generally referring to the average reaction temperature in the dense-phase zone) is 220-280° C., the reaction pressure (generally referring to the pressure in the dense-phase zone) is 0.05-1 MPa (gauge pressure). In addition, the temperature in the vicinity of the gas distributor of the fluidized bed reactor is generally controlled at 320° C. or less.

According to one embodiment of the present invention, as the hydrogenation catalyst, any catalyst used in the art for the hydrogenation reaction of the nitro compound can be enumerated, and at least one selected from a copper-based loaded catalyst, a nickel-based loaded catalyst and a noble metal-based loaded catalyst, more especially a copper-based loaded catalyst can be particularly enumerated. Herein, for the copper-based loaded catalyst, copper is generally used as the main active component, and the support is generally alumina or silica.

According to one embodiment of the present invention, the average particle diameter of the hydrogenation catalyst is generally 30-800 μm, preferably 40-500 μm or 50-600 μm. Preferably, in the hydrogenation catalyst, the catalyst particles having a particle diameter of less than 80 μm comprises not less than 2 wt %, preferably 5-15 wt % by mass percent of all catalyst particles. For example, the average particle diameter can be obtained by the analysis of the sampled solid catalyst particles with a particle-size analyzer.

According to one embodiment of the present invention, the nitro compound is selected from at least one of the compounds represented by the following formula (1), especially nitrobenzene.

$$R-NO_2 \quad (1)$$

According to one embodiment of the present invention, in the structural formula (1), R is an optionally substituted C2-20 straight, branched or cyclic hydrocarbyl, preferably an optionally substituted C4-20 cyclic hydrocarbyl, especially an optionally substituted C6-20 aryl, more especially an optionally substituted phenyl or phenyl.

EXAMPLES

The present invention will be described in further detail below by way of examples and comparative examples, but the present invention is not limited to the following examples.

In the following examples and comparative examples, the expansion coefficient is the ratio of the height of the dense-phase zone in the fluidized bed reactor to the height of the static catalyst bed in the fluidized bed reactor. The height of the dense-phase zone can be obtained with the variance in the axial pressure (gauge pressure) in the fluidized bed reactor.

In the following examples and comparative examples, the instantaneous pressure $P_i$ (the unit is Pa) at a measuring point in the bed is measured by a pressure sensor, and the instantaneous pressure $P_i$ at any time is resolved into the sum of the average value $\bar{p}$ and the fluctuation value p', that is, $P_i = \bar{P} + P'$, the standard deviation Sd at any measuring point is

$$Sd = \sqrt{\frac{1}{N}\sum_{i=1}^{N}(P_i - \bar{P})^2},$$

and N is the number of the sampled data.

Example 1

The fluidized bed reactor for producing aniline by the hydrogenation of nitrobenzene as shown in FIG. 1 was used. A perforated plate as shown in FIG. 2 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10.

The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.06 kg/t aniline, the nitrobenzene content in the crude aniline at the outlet of the fluidized bed was 4.8 mg/kg, and the results were detailed in Table 1.

Example 2

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.07 kg/t aniline, the nitrobenzene content in the crude aniline at the outlet of the fluidized bed was 4.8 mg/kg, and the results were detailed in Table 1.

Example 3

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/5. The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.073 kg/t aniline, the nitrobenzene content in the crude aniline at the outlet of the fluidized bed was 4.8 mg/kg, and the results were detailed in Table 1.

Example 4

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/2. The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.082 kg/t aniline, the nitrobenzene content in the crude aniline at the outlet of the fluidized bed was 4.8 mg/kg, and the results were detailed in Table 1.

Example 5

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.03. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.08 kg/t aniline, the nitrobenzene content in the crude aniline at the outlet of the fluidized bed was 4.8 mg/kg, and the results were detailed in Table 1.

Example 6

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.08. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.1 kg/t aniline, the nitrobenzene content in the crude aniline at the outlet of the fluidized bed was 4.8 mg/kg, and the results were detailed in Table 1.

Example 7

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 5. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.068 kg/t aniline, the nitrobenzene content in the crude aniline at the outlet of the fluidized bed was 4.8 mg/kg, and the results were detailed in Table 2.

Example 8

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 9. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.068 kg/t aniline, the nitrobenzene content in the crude aniline at the outlet of the fluidized bed was 4.8 mg/kg, and the results were detailed in Table 2.

Example 9

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was two, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.063 kg/t aniline, the nitrobenzene content in the crude aniline at the outlet of the fluidized bed was 4.8 mg/kg, and the results were detailed in Table 2.

Example 10

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was four, the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.06 kg/t aniline, the nitrobenzene content in the crude aniline at the outlet of the fluidized bed was 4.8 mg/kg, and the results were detailed in Table 2.

Example 11

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was one, the axial direction height of the perforated plate from the gas distributor at the bottom was 1.2 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.067 kg/t aniline, the nitrobenzene content in the crude aniline at the outlet of the fluidized bed was 4.8 mg/kg, and the results were detailed in Table 2.

Example 12

The fluidized bed reactor for producing aniline by the hydrogenation of nitrobenzene as shown in FIG. 1 was used.

A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.5 times the axial direction height of the dense-phase zone.

The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.075 kg/t aniline, the nitrobenzene content in the crude aniline at the outlet of the fluidized bed was 4.8 mg/kg, and the results were detailed in Table 2.

Example 13

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 300 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.071 kg/t aniline, the nitrobenzene content in the crude aniline at the outlet of the fluidized bed was 4.6 mg/kg, and the results were detailed in Table 3.

Example 14

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 400 μm, and the content of particles lower than 80 μm was 2%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.062 kg/t aniline, the nitrobenzene content in the crude aniline at the outlet of the fluidized bed was 5 mg/kg, and the results were detailed in Table 3.

Example 15

The fluidized bed reactor for producing aniline by the hydrogenation of nitrobenzene as shown in FIG. 1 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The opening rate of the outer edge region was 18%. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone.

The used catalyst was a metal loaded catalyst with copper as the main active component, the support was silica, the catalyst had an average particle diameter of 400 μm, and the content of particles lower than 80 μm was 8%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 0.08 kg/t aniline, the nitrobenzene content in the crude aniline at the outlet of the fluidized bed was 4.3 mg/kg, and the results were detailed in Table 3.

Comparative Example 1

The prior art fluidized bed reactor apparatus for producing aniline by the hydrogenation of nitrobenzene was used, and the difference from that in FIG. 1 lied in no perforated plate was provided. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The catalyst unit consumption was 1.5 kg/t aniline, the nitrobenzene content in the crude aniline at the outlet of the fluidized bed was 4.8 mg/kg, and the results were detailed in Table 3.

Example 16

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate is in a range of 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm.

In all Examples, the length of the upper baffle plate and the length of the lower baffle plate were both 0.6 times the reactor diameter. The height H1 of the first trapezoid was 25 mm, the height H2 of the second trapezoid was 30 mm.

The dense-phase zone in the fluidized bed had a standard deviation of 800 Pa and an expansion coefficient of 1.42, and the results were detailed in Table 4.

Example 17

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 0°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 1050 Pa and an expansion coefficient of 1.35, and the results were detailed in Table 4.

Example 18

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 120°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 1080 Pa and an expansion coefficient of 1.33, and the results were detailed in Table 4.

Example 19

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 0°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 1170 Pa and an expansion coefficient of 1.28, and the results were detailed in Table 4.

Example 20

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 120°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa. The dense-phase zone in the fluidized bed had a standard deviation of 1215 Pa and an expansion coefficient of 1.21, and the results were detailed in Table 4.

Example 21

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 50%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 1030 Pa and an expansion coefficient of 1.36, and the results were detailed in Table 5.

Example 22

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 10%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 980 Pa and an expansion coefficient of 1.35, and the results were detailed in Table 5.

Example 23

The fluidized bed reactor for producing aniline by the hydrogenation of nitrobenzene as shown in FIG. 4 was used.

A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 3%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 975 Pa and an expansion coefficient of 1.37, and the results were detailed in Table 5.

Example 24

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 30%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 1000 Pa and an expansion coefficient of 1.33, and the results were detailed in Table 5.

Example 25

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 2 double-trapezoid structural members, which were divided into one layer. Two double-trapezoid structural members were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 1243 Pa and an expansion coefficient of 1.18, and the results were detailed in Table 5.

Example 26

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 150 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 880 Pa and an expansion coefficient of 1.37, and the results were detailed in Table 6.

Example 27

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 300 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm. The dense-phase zone in the fluidized bed had a standard deviation of 1240 Pa and an expansion coefficient of 1.19, and the results were detailed in Table 6.

Example 28

The fluidized bed reactor for producing aniline by the hydrogenation of nitrobenzene as shown in FIG. 4 was used.

A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 30°, and the vertical distance between the adjacent double-trapezoid structural members in the elevation direction was 150 mm. The dense-phase zone in the fluidized bed had a standard deviation of 910 Pa and an expansion coefficient of 1.36, and the results were detailed in Table 6.

Example 29

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 45°, and the vertical distance between the adjacent double-trapezoid structural members in the elevation direction was 150 mm. The dense-phase zone in the fluidized bed had a standard deviation of 906 Pa and an expansion coefficient of 1.37, and the results were detailed in Table 6.

Example 30

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 60°, and the vertical distance between the adjacent double-trapezoid structural members in the elevation direction was 150 mm. The dense-phase zone in the fluidized bed had a standard deviation of 910 Pa and an expansion coefficient of 1.37, and the results were detailed in Table 6.

Example 31

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 80 mm. The dense-phase zone in the fluidized bed had a standard deviation of 780 Pa and an expansion coefficient of 1.41, and the results were detailed in Table 7.

Example 32

The fluidized bed reactor for producing aniline by the hydrogenation of nitrobenzene as shown in FIG. 4 was used. A perforated plate as shown in FIG. 3 was disposed in the sputtering transition zone of the reactor, and the perforated plate included a center region located at the middle region and an outer edge region disposed at the periphery and surrounding the center region. The ratio of the size of the opening of the outer edge region to the area of the opening of the center region was 1/10. The equivalent diameter of the opening in the outer edge region was 0.005. The radius ratio of the perforated plate to the center region was 2/1. The number of the perforated plate was one, and the axial direction height of the perforated plate from the gas distributor at the bottom was 1.05 times the axial direction height of the dense-phase zone. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of the double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 300 mm. The dense-phase zone in the fluidized bed had a standard deviation of 1220 Pa and an expansion coefficient of 1.20, and the results were detailed in Table 7.

Example 33

The fluidized bed reactor for producing aniline by the hydrogenation of nitrobenzene as shown in FIG. 4 without the perforated plate(s) was used. The used catalyst was a metal loaded catalyst with copper as the main active component, the support was silica, the catalyst had an average particle diameter of 400 μm, and the content of particles lower than 80 μm was 5%. The reaction conditions were as follows: the superficial gas velocity in the fluidized bed reactor was 0.3 m/s, the molar ratio of hydrogen gas to nitrobenzene was 10, the average reaction temperature in the dense-phase zone was controlled at 260° C., the reaction pressure in the dense-phase zone was 0.1 MPa.

The included angle α of two side faces of the upper baffle plate of double-trapezoid structural member was 60°, and the included angle β of two side faces of the lower baffle plate was 90°. The upper baffle plate of the double-trapezoid structural member was provided with opening(s) and/or slit(s) on two side faces, and had an opening rate, i.e., the ratio of the total area of opening(s) and/or slit(s) to the area of the side face of 20%; the lower baffle plate of the double-trapezoid structural member was provided with opening(s) and/or slit(s) on two side faces, and had an opening rate, i.e., the ratio of the total area of opening(s) and/or slit(s) to the area of the side face of 8%. In the dense-phase zone of the fluidized bed reactor were provided 4 double-trapezoid structural members, which were divided into two layers. Two double-trapezoid structural members on each layer were mutually parallel and had a horizontal interval of 100 mm, the double-trapezoid structural members were uniformly distributed in the reactor in a staggered manner, and the included angle in the length direction between any two double-trapezoid structural members positioned in different horizontal planes and adjacent to each other in the vertical direction was 90°, and the vertical distance between the adjacent double-trapezoid structural members in the elevation direction was 150 mm.

The dense-phase zone in the fluidized bed had a standard deviation of 825 Pa and an expansion coefficient of 1.39, and the results were detailed in Table 7.

Comparative Example 4

In the fluidized bed reactor apparatus was provided the grid flow rectifier used in the prior art, the average particle diameter of the catalysts was 400 μm, and other technological conditions are not changed. The dense-phase zone in the fluidized bed had a standard deviation of 1680 Pa and an expansion coefficient of 1.17, and the results were detailed in Table 7.

Comparative Example 5

In the fluidized bed reactor apparatus was provided the large-pore flow rectifier used in the prior art, the average particle diameter of the catalysts was 400 μm, and other technological conditions were not changed. The dense-phase zone in the fluidized bed had a standard deviation of 1660 Pa and an expansion coefficient of 1.18, and the results were detailed in Table 7.

Comparative Example 6

In the fluidized bed reactor apparatus was provided no flow rectifier, namely, free fluidized bed, the average particle diameter of the catalysts was 300 μm, and other technological conditions were not changed. The dense-phase zone in the fluidized bed had a standard deviation of 1810 Pa and an expansion coefficient of 1.05, and the results were detailed in Table 7.

Obviously, the apparatus and the process of the present invention had greater technical advantages and could be used in the industrial production of aniline. They could also be used in other fluidized bed reactors, especially the fluidized bed reactors that are suitable for coarse particles.

TABLE 1

| | Ex. 1 | Ex. 2 | Ex. 3 | Ex. 4 | Ex. 5 | Ex. 6 |
|---|---|---|---|---|---|---|
| Whether the perforated plate is disposed and the type of the structural member | The perforated plate is disposed and the type as shown in FIG. 2 | The perforated plate is disposed and the type as shown in FIG. 3 | The perforated plate is disposed and the type as shown in FIG. 3 | The perforated plate is disposed and the type as shown in FIG. 3 | The perforated plate is disposed and the type as shown in FIG. 3 | The perforated plate is disposed and the type as shown in FIG. 3 |
| Ratio of the size of the opening of the outer edge region to the area of the opening of the center region of the perforated plate | 1/10 | 1/10 | 1/5 | 1/2 | 1/10 | 1/10 |
| equivalent diameter of the opening of the outer edge region, m | 0.005 | 0.005 | 0.005 | 0.005 | 0.03 | 0.08 |
| the radius ratio of perforated plate/center region | 2 | 2 | 2 | 2 | 2 | 2 |
| the number of the perforated plate | 1 | 1 | 1 | 1 | 1 | 1 |
| the ratio of the axial direction height of the perforated plate from the gas distributor at the bottom to the axial direction height of the dense-phase region | 1.05 | 1.05 | 1.05 | 1.05 | 1.05 | 1.05 |
| average particle diameter of the catalyst, μm | 400 | 400 | 400 | 400 | 400 | 400 |
| the content of particles lower than 80 μm | 5 | 5 | 5 | 5 | 5 | 5 |

TABLE 1-continued

|  | Ex. 1 | Ex. 2 | Ex. 3 | Ex. 4 | Ex. 5 | Ex. 6 |
|---|---|---|---|---|---|---|
| catalyst unit consumption, ke/ton aniline | 0.06 | 0.07 | 0.073 | 0.082 | 0.08 | 0.1 |
| The content of nitrobenzene in crude aniline from the fluidized bed outlet, mg/kg | 4.8 | 4.8 | 4.8 | 4.8 | 4.8 | 4.8 |

TABLE 2

|  | Ex. 7 | Ex. 8 | Ex. 9 | Ex. 10 | Ex. 11 | Ex. 12 |
|---|---|---|---|---|---|---|
| Whether the perforated plate is disposed and the type of the structural member | The perforated plate is disposed and the type as shown in FIG. 3 | The perforated plate is disposed and the type as shown in FIG. 3 | The perforated plate is disposed and the type as shown in FIG. 3 | The perforated plate is disposed and the type as shown in FIG. 3 | The perforated plate is disposed and the type as shown in FIG. 3 | The perforated plate is disposed and the type as shown in FIG. 3 |
| Ratio of the size of the opening of the outer edge region to the area of the opening of the center region of the perforated plate | 1/10 | 1/10 | 1/10 | 1/10 | 1/10 | 1/10 |
| equivalent diameter of the opening of the outer edge region, m | 0.005 | 0.005 | 0.005 | 0.005 | 0.005 | 0.005 |
| the radius ratio of perforated plate/center region | 5 | 9 | 2 | 2 | 2 | 2 |
| the number of the perforated plate | 1 | 1 | 2 | 4 | 1 | 1 |
| the ratio of the axial direction height of the perforated plate from the gas distributor at the bottom to the axial direction height of the dense-phase region | 1.05 | 1.05 | 1.05 | 1.05 | 1.2 | 1.5 |
| average particle diameter of the catalyst, μm | 400 | 400 | 400 | 400 | 400 | 400 |
| the content of particles lower than 80 μm | 5 | 5 | 5 | 5 | 5 | 5 |
| catalyst unit consumption, ke/ton aniline | 0.068 | 0.068 | 0.063 | 0.06 | 0.067 | 0.075 |
| The content of nitrobenzene in crude aniline from the fluidized bed outlet, mg/kg | 4.8 | 4.8 | 4.8 | 4.8 | 4.8 | 4.8 |

TABLE 3

|  | Ex. 13 | Ex. 14 | Ex. 15 | Comp Ex. 1 |
|---|---|---|---|---|
| Whether the perforated plate is disposed and the type of the structural member | The perforated plate is disposed and the type as shown in FIG. 2 | The perforated plate is disposed and the type as shown in FIG. 3 | The perforated plate is disposed and the type as shown in FIG. 3 | No perforated plate |
| Ratio of the size of the opening of the outer edge region to the area of the opening of the center region of the perforated plate | 1/10 | 1/10 | 1/10 |  |
| equivalent diameter of the opening of the outer edge region, m | 0.005 | 0.005 | 0.005 |  |
| the radius ratio of perforated plate/center region | 2 | 2 | 2 |  |
| the number of the perforated plate | 1 | 1 | 1 |  |
| the ratio of the axial direction height of the perforated plate from the gas distributor at the bottom to the axial direction height of the dense-phase region | 1.05 | 1.05 | 1.05 |  |

TABLE 3-continued

|  | Ex. 13 | Ex. 14 | Ex. 15 | Comp Ex. 1 |
|---|---|---|---|---|
| average particle diameter of the catalyst, μm | 300 | 400 | 400 | 400 |
| the content of particles lower than 80 μm | 5 | 2 | 8 | 5 |
| catalyst unit consumption, ke/ton aniline | 0.071 | 0.062 | 0.08 | 1.5 |
| The content of nitrobenzene in crude aniline from the fluidized bed outlet, mg/kg | 4.6 | 5 | 4.3 | 4.8 |

TABLE 4

|  | Ex. 16 | Ex. 17 | Ex. 18 | Ex. 19 | Ex. 20 |
|---|---|---|---|---|---|
| Included angle α, ° | 60 | 0 | 120 | 60 | 60 |
| Included angle β, ° | 90 | 90 | 90 | 0 | 120 |
| opening rate of two side faces of the upper baffle plate | 20 | 20 | 20 | 20 | 20 |
| opening rate of two side faces of the lower baffle plate | 8 | 8 | 8 | 8 | 8 |
| The number of the double-trapezoid structural member | 4 | 4 | 4 | 4 | 4 |
| horizontal interval in the double-trapezoid structural member in each layer, mm | 100 | 100 | 100 | 100 | 100 |
| Included angle γ, ° | 90 | 90 | 90 | 90 | 90 |
| vertical distance of adjacent double-trapezoid structural members in the elevation direction, mm | 150 | 150 | 150 | 150 | 150 |
| Standard deviation for bed presure, Pa | 800 | 1050 | 1080 | 1170 | 1215 |
| bed expansion coefficient | 1.42 | 1.35 | 1.33 | 1.28 | 1.21 |

TABLE 5

|  | Ex. 21 | Ex. 22 | Ex. 23 | Ex. 24 | Ex. 25 |
|---|---|---|---|---|---|
| Included angle α, ° | 60 | 60 | 60 | 60 | 60 |
| Included angle β, ° | 90 | 90 | 90 | 90 | 90 |
| opening rate of two side faces of the upper baffle plate | 50 | 10 | 20 | 20 | 20 |
| opening rate of two side faces of the lower baffle plate | 8 | 8 | 3 | 30 | 8 |
| The number of the double-trapezoid structural member | 4 | 4 | 4 | 4 | 2 |
| horizontal interval in the double-trapezoid structural member in each layer, mm | 100 | 100 | 100 | 100 | 100 |
| Included angle γ, ° | 90 | 90 | 90 | 90 | 90 |
| vertical distance of adjacent double-trapezoid structural members in the elevation direction, mm | 150 | 150 | 150 | 150 | 150 |
| Standard deviation for bed presure, Pa | 1030 | 980 | 975 | 1000 | 1243 |
| bed expansion coefficient | 1.36 | 1.35 | 1.37 | 1.33 | 1.18 |

TABLE 6

|  | Ex. 26 | Ex. 27 | Ex. 28 | Ex. 29 | Ex. 30 |
|---|---|---|---|---|---|
| Included angle α, ° | 60 | 60 | 60 | 60 | 60 |
| Included angle β, ° | 90 | 90 | 90 | 90 | 90 |
| opening rate of two side faces of the upper baffle plate | 20 | 20 | 20 | 20 | 20 |
| opening rate of two side faces of the lower baffle plate | 8 | 8 | 8 | 8 | 8 |
| The number of the double-trapezoid structural member | 4 | 4 | 4 | 4 | 4 |
| horizontal interval in the double-trapezoid structural member in each layer, mm | 150 | 300 | 100 | 100 | 100 |
| Included angle γ, ° | 90 | 90 | 30 | 45 | 60 |
| vertical distance of adjacent double-trapezoid structural members in the elevation direction, mm | 150 | 150 | 150 | 150 | 150 |
| Standard deviation for bed presure, Pa | 880 | 1240 | 910 | 906 | 910 |
| bed expansion coefficient | 1.37 | 1.19 | 1.36 | 1.37 | 1.37 |

TABLE 7

|  | Ex. 31 | Ex. 32 | Ex. 32 | Comp Ex. 4 | Comp Ex. 5 | Comp Ex. 6 |
|---|---|---|---|---|---|---|
| Included angle α, ° | 60 | 60 | 60 | Grid-type support body of prior art | Macropore support body of prior art | No support body |
| Included angle β, ° | 90 | 90 | 90 | | | |
| opening rate of two side faces of the upper baffle plate | 20 | 20 | 20 | | | |
| opening rate of two side faces of the lower baffle plate | 8 | 8 | 8 | | | |
| The number of the double-trapezoid structural member | 4 | 4 | 4 | | | |
| horizontal interval in the double-trapezoid structural member in each layer, mm | 100 | 100 | 100 | | | |
| Included angle γ, ° | 90 | 90 | 90 | | | |
| vertical distance of adjacent double-trapezoid structural members in the elevation direction, mm | 80 | 300 | 150 | | | |
| Standard deviation for bed presure, Pa | 780 | 1220 | 825 | 1680 | 1660 | 1810 |
| bed expansion coefficient | 1.41 | 1.20 | 1.39 | 1.17 | 1.18 | 1.05 |

The invention claimed is:

1. A fluidized apparatus, comprising a shell, comprising shell, a gas distributor, and an inner chamber defined by an inner wall of said shell and an upper surface of said gas distributor, said inner chamber has a bottom defined by the upper surface of said gas distributor and a top, wherein along the central axial direction of said fluidized apparatus, assuming the vertical distance between the bottom and the top is H, a region of inner chamber from the bottom and upwards to is the lower region, a region of inner chamber from the top and downward to 0.3H is the upper region, and a region of inner chamber between the lower region and the upper region is the middle region, the height of the middle region along the central axial direction of said fluidized apparatus is 0.005H-0.2H, in the middle region is disposed a perforated plate, the perforated plate comprises an outer edge region and a center region, wherein the opening rate of the outer edge region is A1, the opening rate of the center region is A2 and A1/A2=0.1-0.5, or a ratio of the total opening area of the outer edge region to the total opening area of the center region is 1/10-1/2.

2. The fluidized apparatus according to claim 1, wherein the upper region is a dilute-phase zone, the lower region is a dense-phase zone, the middle region is a particle sputtering transition zone, and/or, the axial direction height of the perforated plate from the upper surface of said gas distributor is 1.05-1.5 times the axial direction height of the dense-phase zone.

3. The fluidized apparatus according to claim 1, wherein the number of the perforated plate is one to five, and a vertical distance between any two adjacent perforated plates along the central axial direction of said fluidized apparatus is 0.001H-0.05H.

4. The fluidized apparatus according to claim 1, wherein straight-line distance between any point on the peripheric edge of the perforated plate and the center point of the perforated plate is R, the region surrounded by all points that are on the perforated plate and away from the center point by the straight-line distance of r is the center region, the region between the center region and the peripheric edge is the outer edge region, then r/R=0.5-0.9 or R/r=2/1-9/1.

5. The fluidized apparatus according to claim 1, wherein the number of center opening(s) in the center region is 1-650 per square meter of the center region, and/or, the number of outer edge opening(s) in the outer edge region is 0-4000 per square meter of the outer edge region, and/or, when there are a plurality of center openings, an equivalent diameter for each of the plurality of center openings is independently 0.04-1 m, and/or, when there are a plurality of outer edge openings, an equivalent diameter for each of the plurality of outer edge openings is independently 0.005-0.2 m, and/or, the opening rate of the outer edge region is 2-40% and the opening rate of the center region is 30-100% , and/or, the perforated plate has a substantially circular shape, the diameter of the circle is 1-10 m, and/or, the thickness of the perforated plate is 5-40 mm.

6. The fluidized apparatus according to claim 1, wherein when the perforated plate is placed horizontally, the shape of the cross-section formed by cutting along the vertical direction a support body separating any two adjacent openings is selected from square, triangle, rhombus, rectangle, circle, ellipse, ring and combinations thereof, or the shape of the cross-section formed by cutting along the vertical direction a support body separating any two adjacent openings is such that substantially no solid particles accumulate on the surface facing towards the upper region of the support body and/or is such that solid particles in contact with the surface facing towards the lower region of the support body are substantially intercepted, or the support body is curved plate-shaped or flat plate-shaped.

7. The fluidized apparatus according to claim 1, wherein the outer edge region and the center region are coaxial with the central axis of the fluidized apparatus, and/or, the peripheric edge of the perforated plate conforms to the shape of the inner wall of the shell of the middle region, and is fixed or connected to the inner wall of said shell, and/or, the peripheric edge of the perforated plate is hermetically combined with the inner wall of the shell of the middle region.

8. The fluidized apparatus according to claim 1, wherein the H is 5-60 m, and/or, the diameter of the lower region is 0.5-12 m, and/or, the diameter of the middle region is 0.5-16 m.

9. The fluidized apparatus according to claim 1, further comprising gas-solid separation device disposed in the upper region and a heat-exchanging device disposed in the lower region, and optionally comprises a double-trapezoid structural member disposed in the lower region.

10. The fluidized apparatus according to claim 9, wherein the double-trapezoid structural member comprises an upper baffle plate, a lower baffle plate, and a connecting piece for fixing the upper baffle plate and the lower baffle plate, the longitudinal section of the upper baffle plate along its central axis is a first trapezoid, the upper base that is a long base and the lower base that is a short base of the first trapezoid are mouth-opened, two side edges mutually form an included angle to each other, the longitudinal section of the lower baffle plate along its central axis is a second trapezoid, the upper base that is a long based and the lower base that is a short based of the second trapezoid are mouth-opened, two side edges mutually form an included angle to each other, the opened mouth of the lower base of the first trapezoid and the opened mouth of the upper base of the second trapezoid are nested with each other.

11. The fluidized apparatus according to claim 10, wherein the central axis of the upper baffle plate is coaxial with the central axis of the lower baffle plate, and/or, the included angle (α) of the two side edges of the upper baffle plate is in the range of 0-120, the included angle (β) of the two side edges of the lower baffle plate is in the range of 0-120°, and/or, the ratio of the length of the short base of the upper baffle plate to the length of the short base of the lower baffle plate is greater than 1, and/or, the vertical distance between the short base of the lower baffle plate and the short base of the upper baffle plate is 0 to less than H1, wherein H1 is the height of the first trapezoid, and/or, the height of the first trapezoid H1 is 20-150 mm, the height of the second trapezoid H2 is 20-150 mm.

12. The fluidized apparatus according to claim 10, wherein a confined or unconfined curved surface is formed by the rotation of the two side edges of the upper baffle plate relative to its central axis, a confined or unconfined curved surface is formed by the rotation of the two side edges of the lower baffle plate relative to its central axis, and/or, the opening rate of the curved surface of the upper baffle plate is 10-50%, the opening rate of the curved surface of the lower baffle plate is 3-30%, or, the two side edges of the upper baffle plate extend along its length direction to form two side faces, the two side edges of the lower baffle plate extend along its length direction to form two side faces, and/or, the opening rate of at least one of the two side faces of the upper baffle plate is 10-50%, the opening rate of at least one of the two side faces of the lower baffle plate is 3-30%, and/or, the size of the upper baffle plate along its length direction is 30-250 mm, the size of the lower baffle plate along its length direction is 30-250 mm.

13. The fluidized apparatus according to claim 9, wherein when the number of the double-trapezoid structural member(s) is 4-240, a plurality of the double-trapezoid structural member are all positioned in the same horizontal plane, each and every positioned in different horizontal planes or any combination thereof, and/or, the included angle in the length direction between any two of the double-trapezoid structural members positioned in different horizontal planes and adjacent to each other in the vertical direction (γ) is 30-90°, and/or, the vertical distance between any two of the double-trapezoid structural members positioned in different horizontal planes and adjacent to each other in the vertical direction H3 is not less than 100 mm, and/or, the horizontal distance between any two adjacent double-trapezoid structural members positioned in the same horizontal plane H4 is not less than 80 mm.

14. A nitro compound hydrogenation reaction process, comprising a step of contacting a nitro compound (especially nitrobenzene) as the reaction raw material and hydrogen gas with a hydrogenation catalyst to obtain a reaction product (for example an amino compound, especially aniline) (referred to as a hydrogenation reaction step), wherein the hydrogenation reaction step is carried out in the fluidized bed reactor according to claim 1.

15. The hydrogenation reaction process according to claim 14, wherein the reaction conditions of the hydrogenation reaction comprise: the superficial gas velocity is 0.2-0.8 m/s, the molar ratio of hydrogen gas to the reaction raw material is 6-21, the reaction temperature is 220-280° C., the reaction pressure is 0.05-1 MPa of gauge pressure, the hydrogenation catalyst is selected from at least one of a copper-based loaded catalyst, a nickel-based loaded catalyst and a noble metal-based loaded catalyst, and/or, the bulk density of the hydrogenation catalyst is 300-1200 kg/m³, and/or, the average particle diameter of the hydrogenation catalyst is 30-800 μm, and catalyst particles having a particle diameter of less than 80 μm comprise not less than 2 wt % by mass percent of all catalyst particles, and/or, the nitro compound is selected from at least one of the compounds of formula (1),

R—NO₂        (1)

wherein in formula (1), R is an optionally substituted C2-20 straight, branched or cyclic hydrocarbyl.

16. The fluidized apparatus according to claim 1, the fluidized apparatus is a fluidized bed reactor, and/or, the perforated plate is selected from at least one of punched-plate, screen mesh and grid, and/or, the ratio of the total opening area of the outer edge region to the total opening area of the center region is 1/5-1/2.

17. the fluidized apparatus according to claim 4, wherein R is a radius, and/or, r/R=0.7-0.85, and/or R/r=2/1-5/1.

18. The fluidized apparatus according to claim 5, wherein the number of center opening(s) in the center region is 15-150 per square meter of the center region, and/or, the number of outer edge opening(s) in the outer edge region is 200-500 per square meter of the outer edge region, and/or, the opening rate of the outer edge region is 8-20%, and the opening rate of the center region is 40-80%, and/or, the perforated plate has a substantially circular shape, the diameter of the circle is 2-5 m, and/or the thickness of the perforated plate is 10-35 mm.

19. The fluidized apparatus according to claim 6, wherein the support body is arranged vertically or arranged inclined from the vertical direction towards the lower region, and/or the support boody is arrange inclined at 10-20°.

20. The fluidized apparatus according to claim 7, wherein the H is 10-30 m, and/or, the diameter of the lower region is 1-8 m, and/or, the diameter of the middle region is 1-10 m.

21. The fluidized apparatus according to claim 10, wherein the opened mouth of the upper base of the second trapezoid is nested in the opened mouth of the lower base of the first trapezoid.

22. The fluidized apparatus according to claim 11, wherein the included angle (α) of the two side edges of the upper baffle plate is in the range of 0-60°, and/or the included angle (β) of the two side edges of the lower baffle plate is in the range of 45-90°, and/or, the ratioin of the length of the short base of the upper baffle plate to the length of the short base of the lower baffle plate is 1.1-3, and/or, the vertical distance between the short base of the lower baffle plate and the short base of the upper baffle plate is 0.01H1 to 0.5H1.

23. The fluidized apparatus according to claim 13, wherein the number of the double-trapezoid structural member(s) is 10-120.

24. The hydrogenation reaction process according to claim 14, wherein the nitro compound is nitrobenzene, and the reaction product is aniline.

25. The hudrogenation reaction process according to claim 15, wherein the average particle diameter of the hydrogentaton catalyst is 40-500 μm, and/or, the catalyst particles having a particle diameter of less then 80 μm comprise 5-15 wt % by mass percent of all catalyst particles, and/or, R is an optionally substituted C4-20cyclic hydrocarbyl, or an optioinally substituted C6-20 aryl, or an optionally substituted phenyl.

26. A double-trapezoid structural member, comprising an upper baffle plate, a lower baffle plate and a connecting piece for fixing the upper baffle plate and the lower baffle plate, the longitudinal section of the upper baffle plate along its central axis is a first trapezoid, an upper base that is a long based and a lower base that is a short base of the first trapezoid are mouth-opened, two side edges mutually form an included angle to each other, the longitudinal section of the lower baffle plate along its central axis is a second trapezoid, an upper base that is a short base and a lower base that is a long base of the second trapezoid are mouth-opened, two side edges mutually form an included angle to each other, the opened-mouth of the lower base of the first trapezoid and the opened mouth of the upper base of the second trapezoid are nested with each other.

27. The double-trapezoid structural member according to claim 26, wherein the central axis of the upper baffle plate is coaxial with the central axis of the lower baffle plate, and/or, the included angle ($\alpha$) of the two side edges of the upper baffle plate is in the range of 0-120°, the included angle ($\beta$) of the two side edges of the lower baffle plate is in the range of 0-120°, and/or, the ratio of the length of the short base of the upper baffle plate to the length of the short base of the lower baffle plate is greater than 1, and/or, the vertical distance between the short base of the lower baffle plate and the short base of the upper baffle plate is 0 to less than H1, wherein H1 is the height of the first trapezoid, and/or, the height of the first trapezoid H1 is 20-150 mm, the height of the second trapezoid H2 is 20-150 mm.

28. The double-trapezoid structural member according to claim 26, wherein a confined or unconfined curved surface is formed by the rotation of the two side edges of the upper baffle plate relative to its central axis, a confined or unconfined curved surface is formed by the rotation of the two side edges of the lower baffle plate relative to its central axis, and/or, the opening rate of the curved surface of the upper baffle plate is 10-50%, the opening rate of the curved surface of the lower baffle plate is 3-30%, or, the two side edges of the upper baffle plate extend along its length direction to form two side faces, the two side edges of the lower baffle plate extend along its length direction to form two side faces, and/or, the opening rate of at least one of the two side faces of the upper baffle plate is 10-50%, the opening rate of at least one of the two side faces of the lower baffle plate is 3-30%, and/or, the size of the upper baffle plate along its length direction is 30-250 mm, the size of the lower baffle plate along its length direction is 30-250 mm.

29. A fluidized bed reactor, comprising a shell, a gas distributor, and an inner chamber defined by an inner wall of said shell and an upper surface of said gas distributor, wherein in said inner chamber is disposed the double-trapezoid structural member according to claim 26.

30. A nitro compound hydrogenation reaction process, comprising a step of contacting a nitro compound (especially nitrobenzene) as the reaction raw material and hydrogen gas with a hydrogenation catalyst to obtain a reaction product (for example an amino compound, especially aniline) (referred to as a hydrogenation reaction step), wherein the hydrogenation reaction step is carried out in the fluidized bed reactor according to claim 17.

31. The double-trapezoid structural member according to claim 26, wherein the opened mouth of the upper base of the second trapezoid is nested in the opened-mouth of the lower base of the first trapezoid.

32. The double-trapezoid structural member according to claim 27, wherein the included angle ($\alpha$) of the two side edges of the upper baffle plate is in the range of 0-60°, and/or the included angle ($\beta$) of the two side edges of the lower baffle plate is in the range of 45-90°, and/or, the ratio of the length of the short base of the upper baffle plate to the length of the short base of the lower baffle plate is 1.1-3, and/or, the vertical distance between the short base of the lower baffle plate and the short base of the upper baffle plate is 0.01H1 to 0.5H1.

* * * * *